US007329511B2

(12) United States Patent
Tobin et al.

(10) Patent No.: US 7,329,511 B2
(45) Date of Patent: *Feb. 12, 2008

(54) NUCLEIC ACID ENCODING GAD65

(75) Inventors: Allan J. Tobin, Los Angeles, CA (US); Mark G. Erlander, Tarzana, CA (US); Daniel L. Kaufman, Santa Monica, CA (US)

(73) Assignee: The Regents of The University of California, Oakland, CA (US)

( * ) Notice: Subject to any disclaimer, the term of this patent is extended or adjusted under 35 U.S.C. 154(b) by 525 days.

This patent is subject to a terminal disclaimer.

(21) Appl. No.: 10/641,149

(22) Filed: Aug. 15, 2003

(65) Prior Publication Data

US 2005/0164342 A1 Jul. 28, 2005

Related U.S. Application Data

(63) Continuation of application No. 07/586,536, filed on Sep. 21, 1990, now Pat. No. 6,682,906.

(51) Int. Cl.
*C12P 21/06* (2006.01)
(52) U.S. Cl. .................... 435/69.1; 435/6; 435/69.1; 435/69.3; 435/320.1; 435/252.3; 435/325; 536/23.1; 530/350
(58) Field of Classification Search .............. None
See application file for complete search history.

(56) References Cited

U.S. PATENT DOCUMENTS

| 4,487,830 A | 12/1984 | Coates et al. |
| 4,751,181 A | 6/1988 | Keene |
| 5,792,620 A | 8/1998 | Lernmark et al. |
| 5,998,366 A | 12/1999 | Tobin et al. |

FOREIGN PATENT DOCUMENTS

| EP | 0 383 129 | 8/1990 |
| WO | 90/07117 | 6/1990 |
| WO | 92/05446 | 4/1992 |

OTHER PUBLICATIONS

T.A. M.A. Al-Bukhari et al., "*Distinct antigenic features of linear epitopes at the N-terminus and C-terminus of 65 kDa glutmamic acid decarboxylase (GAD65): implications for autoantigen modification during pathogenesis,*" 130 Clin. Exp. Immunol. 131-139 (2002).

J-M. Bach et al., "*High Affinity Presentation of an Autoantigenic Peptide in Type I Diabetes by an HLA Class II Protein Encoded in a Haplotype Protecting From Disease,*" 10 Journal of Autoimmunity 375-386 (1997).

A. Falorni et al., in "*Diagnostic sensitivity of immunodominant epitopes of glutamic acid decarboxylase (GAD65) autoantibodies in childhood IDDM,*" 39 DIABETOLOGIA 1091-1098 (1996).

E. Harfouch-Hammoud et al., in "Identification of Peptides From Autoantigens GAD65 and IA-2 That Bind to HLA Class II Molecules Predisposing to or Protecting From Type 1 Diabetes," 48 Diabetes 1937-1947 (Oct. 1999).

D. Kaufman et al., "Autoimmunity to Two Forms of Glutamate Decarboxylase in Insulin-dependent Diabetes Mellitus," 89 J. Clin. Invest. 283-292 (Jan. 1992).

T. Kobayashi et al., in "*Unique Epitopes of Glutamic Acid Decarboxylase Autoantibodies in Slowly Progressive Type 1 Diabetes,*" 88(10) The Journal of Clinical Endocrinology & Metabolism 4768-4775 (2003).

L. Li et al., "*Differential Detection of Rat Islet and Brain Glutamic Acid Decarboxylase (GAD) Isoforms with Sequence-specific Peptide Antibodies,*" 43(1) The Journal of Histochemistry and Cytochemistry 53-59 (1995).

T. Lohmann et al., "*Humoral and Cellular Autoimmune Responses in Stiff person Syndrome,*" 998 Ann. N.Y. Acad. Sci. 998 215-222 (2003).

T. Lohmann et al., "*Immunodominant epitopes of glutamic acid decarboxylase 65 and 67 in insulin-dependent diabetes mellitus,*" 343 The Lancet 1607-1608 (Jun. 25, 1994).

T. Lohmann et al., "*T cell Clones to Epitopes of Glutamic Acid Decarboxylase 65 Raised from Normal Subjects and Patients with Insulin-dependent Diabetes,*" 9 Journal of Autoimmunity 385-389 (1996).

M.A. Myers et al., "*A Diabetes-Related Epitope of GAD65: A Major Diabetes-Related Conformational Epitope on GAD65,*" 1005 Annals of the New York Academy of Sciences 250-252 (2003).

P. Panina-Bordignon et al., "*Cytotoxic T Cells Specific For Glutamic Acid Decarboxylase in Autoimmune Diabetes,*" J. Exp. Med. 1923-1927 (May 1995).

Salil D. Patel et al. in "*Identification of Immunodominant T cell epitopes of human glutamic acid decarboxylase 65 by using HLA-DR ($\alpha*0101,\beta1*0401$) transgenic mice.*" 94 Proc. Natl. Acad. Sci. USA 8082-87 (Jul. 1997).

A. C. Powers et al., "*Comparative analysis of epitope recognition of glutamic acid decarboxylase (GAD) by autoantibodies from different autoimmune disorders,*" 118 Clinical and Experimental Immunology 349-356 (1999).

Anthony Quinn & Eli E. Sercarz, "*T Cells with Multiple Fine Specificities are Used by Non-obese Diabetic (NOD) Mice in the Response to GAD(524-543),*" 9 Journal of Autoimmunity 365-370 (1996).

(Continued)

*Primary Examiner*—Hope Robinson
(74) *Attorney, Agent, or Firm*—Erin M Dunston; Bingham McCutchen LLP

(57) ABSTRACT

The invention provides cDNA molecules comprising a part of the cDNA sequence of $GAD_{65}$ which encode at least one epitope for autoantibodies to $GAD_{65}$. The invention also provides cloning vehicles capable of replication and expression comprising cDNA molecules coding for $GAD_{65}$. The invention further provides for hosts transformed with a vehicle having a cDNA molecule coding for $GAD_{65}$. In another embodiment, the invention provides for the detection of autoantibodies to $GAD_{65}$ using the $GAD_{65}$ polypeptides coded for by the cDNA molecules of the invention.

6 Claims, 13 Drawing Sheets

OTHER PUBLICATIONS

F. Rharbaoui et al., in "*Peptide specificity of high-titer anti-glutamic acid decarboxylase (GAD)65 autoantibodies,*" 62 Immunology Letters 123-130 (1998).

Y. Shi et al., "*Amino Acid Residues 24-31 but not Palmitoylation of Cysteines 30 and 45 Are Required for Membrane Anchoring of Glutamic Acid Decarboxylase, GAD$_{65}$,*" 124(6) The Journal of Cell Biology 927-934 (Mar. 1994).

M. Solimena et al., "*A Signal Located within Amino Acids 1-27 of GAD65 Is Required for Its Targeting to the Golgi Complex Region,*" 126(2) The Journal of Cell Biology 331-341 (Jul. 1994).

K. Syren et al., "*Immune Reactivity of Diabetes-Associated Human Monoclonal Autoantibodies Defines Multiple Epitopes and Detects Two Domain Boundaries in Glutamate Decarboxylase,*" The Journal of Immunology 5208-5214 (1996).

M. A. Zechel et al., in "*Characterization of Novel T-Cell Epitopes on 65 kDa and 67 kDa Glutamic Acid Decarboxylase Relevant in Autoimmune Responses in NOD Mice,*" 11 Journal of Autoimmunity 83-95 (1998).

Persson, et al., Expression of the Neurotransmitter-Synthesizing Enzyme Glutamic Acid Decarboxylase in Male Germ Cells; Molecular and Cellular Biology, pp. 4701-4711, Sep. 1990, vol. 10, No. 9.

Julien, et al. Rat Brain Glutamic Acid Decarboxylase Sequence Deduced from a Cloned cDNA; Journal of Neurochemistry, 54:703-705, 1990.

Legay, et al., Evidence for Two Distinct Forms of Native Glutamic Acid Decarboxylase in Rat Brain Soluble Extract: An Immunoblotting Study; Journal of Neurochemistry, 48:1022-1026, 1987.

Michelsen, et al., Cloning, characterization, and autoimmune recognition of rat islet glutamic acid decarboxylase in insulin-dependent diabetes mellitus, Proc. Natl. Acad. Sci. USA, vol. 88, pp. 8754-8758, Oct. 1991.

Julien, et al., Molecular Cloning, Expression and in situ Hybridization of Rat Brain Glutamic Acid Decarboxylase Messenger RNA; Neuroscience Letters, 73:173-180, 1987.

Kobayashi, et al., Glutamic Acid Decarboxylase cDNA; Nucleotide Sequence Encoding an Enzymatically Active Fusion Protein; The Journal of Neuroscience, 7(9)2768-2772, 1987.

Solimena, et al., Autoantibodies to Gaba-Ergic Neurons and Pancreatic Beta Cells in Stiff-Man Syndrome: The New England Journal of Medicine, vol. 322, No. 22, pp. 1555-1560, May 1990.

Baekkeskov, et al., Identification of the 65K Autoantigen in Insulin-Dependent Diabetes as the GABA-synthesizing Enzyme Glutamic Acid Decarboxylase; Nature, vol. 347, 151-156, 1990.

Atkinson, et al., What Causes Diabetes? Scientific American, pp. 62-71, 1990.

Baekkeskov, et al., Revelation of Specificity of 64K Autoantibodies in IDDM Serums by High-Resolution 2-D Gel Electrophoresis; Diabetes, vol. 38;1133-1141, 1989.

Baekkesov, et al., Autoantibodies in Newly Diagnosed Diabetic Children Immunoprecipitate Human Pancreatic Islet Cell Proteins; Nature, 298:167-169, 1982.

Baekkeskov, et al., Antibodies to a 64,000 M, Human Islet Cell Antigen Precede the Clinical Onset of Insulin-Dependent Diabetes; J. Clin. Invest., 79:926-934, 1987.

Chang, et al., Characterization of the Proteins Purified with Monoclonal Antibodies to Glutamic Acid Decarboxylase; The Journal of Neuroscience, 8(6):2123-2130, 1988.

Zielger, et al. Predicting Type I Diabetes; Diabetes Care, 13:762-775, 1990.

Christie, et al., Characterization of a cDNA Coding for Rat Glutamic Acid Decarboxylase; Molecular Brian Research 8:193-198, 1990.

Atkinson, et al., 64000 M, Autoantibodies as predictors of Insulin-Dependent Diabetes; The Lancet, vol. 335:1357-1360, 1990.

Christie, et al., Cellular and Subcellular Localization of an M, 64,000 Protein Autoantigen in Insulin-Dependent Diabetes; The Journal of Biological Chemistry, 265(1) 376-381 (1990).

Katarova, et al., Molecular Identification of the 62 kd Form of Glutamic Acid Decarboxylase from the Mouse; European Journal of Neuroscience, vol. 2, No. 3, pp. 190-202, 1990.

Wyborski, et al., Characterization of CDNA Coding for Rat Glutamic Acid Decarboxylase; Molecular Brain Research, 8:193-198, 1990.

Kaufman, et al., Brain Glutamate Decarboxylase Cloned in λgt-11: Fusion Protein Produces λ-Aminobutyric Acid; Science vol. 232:1138-1140, 1986.

Bu, et al., Two Human Glutamate Decarboxylases, 65-kDa GAD and 67-kDa GAD, Are each Encoded by a Single Gene, Proceedings of the National Academy of Sciences, vol. 89, No. 6, pp. 2115-2119, 1992.

Karlsen, et al., Cloning and Primary Structure of a Human Islet Isoform of Glutamic Acid Decarboxylase from Chromosomo 10, Proceedings of the National Academy of Sciences, vol. 88, No. 19, pp. 8337-8341, 1991.

Karlsen, et al., Immune Recognition and Gene Expression of Islet Glutamic Acid Decarboxylase, Clinical Research, vol. 39, No. 2, p. 173A, 1991.

Expression of Cloned Genes in Cultured Mammalian Cells, 16.1-16.56, 1989; Sambrook, et al.

Detection and Analysis of Proteins Expressed from Cloned Genes, 18.1-18.26, 1989, Sambrook et al.

Mulligan et al., Selection for Animal Cells That Express the *Escherichia coli* Gene Coding for Xanthine-Guanine, Proceedings of the National Academy of Sciences, vol. 78, No. 4, pp. 2072-2076, 1981.

Kingsman et al., The Production of Mammalian Proteins in *Saccharomyces cerevisiae*, T/BTECH, pp. 53-57, 1987.

Howell et al., Vaccination Against Experimental Allergic Encephalomyelitis with T Cell Receptor Peptides, Science, vol. 246, pp. 668-670, 1989.

Wraith et al., Antigen Recognition in Autoimmune Encephalomyelitis and the Potential for Peptide-Mediated Immunotherapy, Cell. vol. 59, pp. 247-255, 1989.

Huang et al., Molecular Cloning and Amino Acid Sequence of Brain L-glutamate Decarboxylase, Proceedings of the National Academy of Sciences, vol. 87, pp. 8491-8495, 1990.

Baekkeskov et al., Autoantibodies to a 64-kilodalton Islet Cell Protein Precede the Onset of Spontaneous Diabetes in the BB Rat, Science, vol. 224, pp. 1348-1350, 1984.

Gerling et al., Islet Cell and 64K Autoantibodies are Associated with Plasma IgG in Newly Diagnosed Insulin-Dependent Diabetic Children, vol. 137, No. 12, pp. 3782-3785, 1986.

Atkinson, et al. Autoantibodies in Nonobese Diabetic Mice Immunoprecipitate 64,000-*M*, Islet antigen, Diabetes, vol. 37, pp. 1587-1590, 1988.

Tuomi et al., Antibodies to Glutamic Acid Decarboxylase Reveal Latent Autoimmune Diabetes Mellitus in Adults With a Non-Insulin-Dependent Onset of Disease, Diabetes, vol. 42, pp. 359-362, 1993.

Zimmet et al., Crucial Points at Diagnosis Type 2 diabetes or slow type 1 diabetes, Diabetes Care, vol. 22, Supplement 2, pp. B59-B64, 1999.

Schranz et al., Immunology in diabetes: an update, Diabetes Metab. Rev. vol. 14, No. 1, pp. 3-29, 1998.

Hagopian et al., Quantitative Assay Using Recombinant Human Islet Glutamic Acid Decarboxylase (GAD65) Shows That 64K Autoantibody Positivity at Onset Predicts Type, J. Clin. Invest., vol. 91, pp. 368-374, 1993.

Zimmet et al., Antibodies to glutamic acid decarboxylase in the prediction of insulin dependency, Diabetes Res. Clin. Pract., vol. 34, pp. S125-131, 1996.

Zimmet et al., Latent autoimmune diabetes mellitus in adults (LADA): the role of antibodies to glutamic acid decarboxylase in diagnosis and prediction of insulin dependency, Diabet. Med. vol. 11, No. 3, pp. 299-303, 1994 (abstract).

```
GGGCGTGCGGGGTCGAGCCGAAGCAGCTTGCCCGCAGCCACTCGGAGGCGACCAGCGCCA
         10                  20          30            40            50
GACTAGCAGAACCCATGGCATCTCCGGGTCTCTGGCTTTTGGTCCTTCGGATCTGAAGATG
                M   A   S   P   G   S   W   F   G   S   E   D   G
         70                  80          90            100           110
GCTCTGGGGATCCTGAGAACAGCCGGGAACAGCGAGAGCCTGGTGTGCCAGGTGCCCAAAAGT
 S   G   D   P   E   N   P   G   T   A   R   A   W   C   Q   V   A   Q   K   F
         130                 140         150           160           170
TCACGGGCGGCATCGGAAAACAAGCTATGCGCTCTGCTCTACGGAGACTCTGAGAAGCCAG
 T   G   G   I   G   N   K   L   C   A   L   L   Y   G   D   S   E   K   P   A
         190                 200         210           220           230
CAGAGAGCGGCGGGAGCGTGACCTCGCGGGCCGCCACTCGGAAGGTCGCCTGCACCTGTG
 E   S   G   G   S   V   T   S   R   A   A   T   R   K   V   A   C   T   C   D
         250                 260         270           280           290
ACCAAAAACCCTGCAGCTGCCCCAAAGGAGATGTCAATTATGCACTTCTCCACGCAACAG
 Q   K   P   C   S   C   P   K   G   D   V   N   Y   A   L   H   A   T   D
         310                 320         330           340           350
ACCTGCTGCCAGCCCTGTGAAGGAGAAAGGCCCACTCTGCATTTCTGCAAGATGTAATGA
 L   L   P   A   C   E   G   E   R   P   T   L   A   F   L   Q   D   V   M   N
         370                 380         390           400           410
ACATTTGCTTCAGTACGTGGTGAAAAGTTTGATAGATCAACTAAAGTGATTGATTTCC
 I   L   Q   Y   V   V   K   S   F   D   R   S   T   K   V   I   D   F   H
         430                 440         450           460           470
ATTACCCCAATGAGCTTCTTCAAGAGTATAATTGGGAATTGGCAGACCAACCGCAAAATC
 Y   P   N   E   L   L   Q   E   Y   N   W   E   L   A   D   Q   P   Q   N   L
         490                 500         510           520           530
                E   I   L   T   H   C   Q   T   T   L   K   Y   A   I   K   T   G   H   P
```

Figure 2A

```
TGGAGGAAATTTGACGCACTGCCAAACAACTCTAAAATATGCGATTAAAACAGGGCATC
         550                 570                 590
  R   Y   F   N   Q   L   S   T   G   L   D   M   V   G   L   A   A   D   W   L
CCCGATATTTTAATCAGCTGTCTACCGGATTGGATATGGTTGGATTAGCAGCAGATTGGT
         610                 630                 650
  T   S   T   A   N   T   N   M   F   T   Y   E   I   A   P   V   F   V   L   L
TGACATCAACAGCAAACACGAACATGTTTACCTATGAGATCGCCCCTGTATTTGTACTAC
         670                 690                 710
  E   Y   V   T   L   K   K   M   R   E   I   I   G   W   P   G   G   S   G   D
TGGAATATGTGACACTAAAGAAAATGAGGGAAATCATTGGCTGGCCAGGAGGCTCTGGCG
         730                 750                 770
  G   I   F   S   P   G   G   A   I   S   N   M   Y   A   M   L   I   A   R   Y
ATGGAATCTTTTCTCCTGGTGTGCCATCTCCAACATGTACGCCATGCTCATTGCCCGCT
         790                 810                 830
  K   M   F   P   E   V   K   E   K   G   M   A   A   V   P   R   L   I   A   F
ATAAGATGTTTCCAGAAGTCAAGGAAAAGGGGATGGCGGTGCCCAGGCTCATCGCCAT
         850                 870                 890
  T   S   E   H   S   H   F   S   L   K   K   G   A   A   A   L   G   I   G   T
TCACGTCAGAGCATAGTCACTTTTCTCTCAAGAAGGGAGCTGCAGCCTTGGGGATCGGAA
         910                 930                 950
  D   S   V   I   L   I   K   C   D   E   R   G   K   M   I   P   S   D   L   E
CAGACAGCGTGATTCTGATTAAATGTGATGAGAGAGGGAAAATGATCCCATCTGACCTTG
         970                 990                1010
  R   R   I   L   E   V   K   Q   K   G   F   V   P   F   L   V   S   A   T   A
AAAGAAGAATCCTTGAAGTCAAACAGAAAGGATTTGTTCCTTTCCTGGTGAGTGCCACAG
        1030                1050                1070
  G   T   T   V   Y   G   A   F   D   P   L   L   A   V   A   D   I   C   K   K
```

Figure 2B

```
CTGGAACCACTGTGTACGGGGCTTTTGATCCTCTCTTGGCTGTAGCTGACATCTGCAAAA
         1090                 1110                 1130
 L  E  P  L  C  T  G  A  F  D  P  L  L  A  V  A  D  I  C  K
AATATAAGATCTGGATGCATGTGGATGCAGCTTGGGGGTGGAGGGTTACTGATGTCTCGGA
         1150                 1170                 1190
  Y  K  I  W  M  H  V  D  A  A  W  G  G  G  L  L  M  S  R  K
AACACAAGTGGAAGCTGAACGGTGTGTGGAGAGGGCCAACTCTGTGACATGGAATCCCACA
         1210                 1230                 1250
 H  K  W  K  L  N  G  V  E  R  A  N  S  V  T  W  N  P  H  K
AGATGATGGGTGTCCCCTTGCAATGTTCGGCTCTCCTGGTCAGAGAGGAGGACTGATGC
         1270                 1290                 1310
  M  M  G  V  P  L  Q  C  S  A  L  L  V  R  E  E  G  L  M  Q
AGAGCTGCAACCAGATGCATGCTTCCTACCTCTTCAGCAAGATAAGCACTATGACCTGT
         1330                 1350                 1370
 S  C  N  Q  M  H  A  S  Y  L  F  Q  Q  D  K  H  Y  D  L  S
CCTATGACACGGGAGACAAGGCCTTGCAGTGTGACGCCACGTCGATGTCTTTAAATTAT
         1390                 1410                 1430
  Y  D  T  G  D  K  A  L  Q  C  G  R  H  V  D  V  F  K  L  W
GGCTCATGTGGAGAGAGCAAAGGGACTACTGGATTGAAGCTCACATTGATAAGTGTTTGG
         1450                 1470                 1490
 L  M  W  R  A  K  G  T  T  G  F  E  A  H  I  D  K  C  L  E
AGCTGGCAGAGTATTTATACAATATCATTAAAAACCGAGAAGGATATGAAATGGTGTTCG
         1510                 1530                 1550
  L  A  E  Y  L  Y  N  I  I  K  N  R  E  G  Y  E  M  V  F  D
ATGGGAAGCCTCAGCACACAAATGTCTGCTTCTGGTTTGTACCTCCTAGTTTGCGAGTTC
         1570                 1590                 1610
 G  K  P  Q  H  T  N  V  C  F  W  F  V  P  P  S  L  R  V  L
                 E  D  N  E  E  R  M  S  R  L  S  K  V  A  P  V  I  K  A  R

Figure 2C
```

```
TGGAAGACAATGAAGAGAGAATGAGCCGCCTCTCAAAGGTGGCGCCAGTGATTAAAGCCA
 M  E  Y  G  T  T  M  V  S  Y  Q  P  L  G  D  K  V  N  F
          1630                 1650                 1670
GAATGATGGAGTATGGGACCACAATGGTCAGCTACCAACCCTTAGGAGATAAGGTCAACT
 F  R  M  V  I  S  N  P  A  A  T  H  Q  D  I  D  F  L  I  E
          1690                 1710                 1730
TCTTCCGCATGGTCATCTCAAACCCTGCAGCAACTCACCAAGACATTGACTTCCTCATTG
 E  I  E  R  L  G  Q  D  L  *
          1750                 1770                 1790
AAGAAATCGAACGCCTGGGACAAGATTTGTAATCACTTTGCTCACCAAACTTTCAGTTCT
          1810                 1830                 1850
CTAGGTAGACAGCTAAGTTGTCACAAACTGTAAATGTATTTGTAGTTTGTTCCAGAGT
          1870                 1890                 1910
AATTCTATTTCTATATCGTGGTGTCACAGTAGAGTCCAGTTTAAAA
          1930                 1950
```

Figure 2D

```
                                                                    M  A  S
AGCTCGCCCGCAGCTCGCACTCGGCAGGCGACCTGCTCCAGTCTCCAAAGCCGATGGCATC
         10                  20                  30                  40                  50
 P  G  S  G  F  W  S  F  G  S  E  D  G  S  G  D  S  E  N  P
TCCGGGGCTCTGGCTTTTGGTCTTTCGGGTCGGAAGATGGCTCTGGGGATTCCGAGAATCC
         70                  90                                                            110
 G  T  A  R  A  W  C  Q  V  A  Q  K  F  T  G  G  I  G  N  K
CGGCACACAGGCGCGAGCCTGGTGCCAAGTGGCTCAGAAGTTCACGGGCGGCATCGGAAACAA
        130                 150                                                           170
 L  C  A  L  L  Y  G  D  A  E  K  P  A  E  S  G  G  S  Q  P
ACTGTGCGCCCTGCTCTACGGAGACGCCGAGAAGCCGGCGGAGAGCGGGGGAGCCAACC
        190                 210                                                           230
 P  R  A  A  A  R  K  A  A  C  A  C  D  Q  K  P  C  S  C  S
CCCGCGGGCGGCCGCCCGGAAGGCCGCCTGCGCCTGCGACCAGAAGCCCTGCAGCTGCTC
        250                 270                                                           290
 K  V  D  V  N  Y  A  F  L  H  A  T  D  L  L  P  A  C  D  G
CAAAGTGGATGTCAACTACGCGTTTCTCCATGCAACAGACCTGCTGCCGGCGTGTGATGG
        310                 330                                                           350
 E  R  P  T  L  A  F  L  Q  D  V  M  N  I  L  L  Q  Y  V  V
AGAAAGGCCCACTTTGGCGTTTCTGCAAGATGTTATGAACATTTTACTTCAGTATGTGGT
        370                 390                                                           410
 K  S  F  D  R  S  T  K  V  I  D  F  H  Y  P  N  E  L  L  Q
GAAAAGTTTCGATAGATCAACCAAAGTGATTGATTTCCATTATCCTAATGAGCTTCTCCA
        430                 450                                                           470
 E  Y  N  W  E  L  A  D  Q  P  Q  N  L  E  E  I  L  M  H  C
AGAATATAATTGGGAATTGGCAGACCAACCACAAAATTTGGAGGAAATTTTGATGCATTG
```

Figure 3A

```
      490                     510                         530
  Q   T   L   K   Y   A   I   K   T   G   H   P   R   Y   F   N   Q   L   S
Q CCAAACAACTCTAAAATATGCAATTAAAACAGGGCATCCTAGATACTTCAATCAACTTTC
      550                     570                         590
  T   G   L   D   M   V   G   L   A   A   D   W   L   T   S   T   A   N   T   N
TACTGGTTTGGATATGGTTGGATTAGCAGCAGACTGGCTGACATCAACAGCAAATACTAA
      610                     630                         650
  M   F   T   Y   E   I   A   P   V   F   V   L   L   E   Y   V   T   L   K   K
CATGTTCACCTATGAAATTGCTCCAGTATTTGTGCTTTTGGAATATGTCACACTAAAGAA
      670                     690                         710
  M   R   E   I   I   G   W   P   G   G   S   G   D   G   I   F   S   P   G   G
AATGAGAGAAATCATTGGCTGGCCAGGGGCTCTGGCGATGGGATATTTTCTCCCGGTGG
      730                     750                         770
  A   I   S   N   M   Y   A   M   M   I   A   R   F   K   M   F   P   E   V   K
CGCCATATCTAACATGTATGCCATGATGATCGCACGCTTTAAGATGTTCCCAGAAGTCAA
      790                     810                         830
  E   K   G   M   A   A   L   P   R   L   I   A   F   T   S   E   H   S   H   F
GGAGAAAGGAATGGCTGCTCTTCCCAGGCTCATTGCCTTCACGTCTGAACATAGTCATTT
      850                     870                         890
  S   L   K   K   G   A   A   A   L   G   I   G   T   D   S   V   I   L   I   K
TTCTCTCAAGAAGGGAGCTGCAGCCTTAGGGATTGGAACAGACAGCGTGATTCTGATTAA
      910                     930                         950
  C   D   E   R   G   K   M   I   P   S   D   L   E   R   R   I   L   E   A   K
ATGTGATGAGAGGGAAAATGATTCCATCTGATCTTGAAAGAAGGATTCTTGAAGCCAA
      970                     990                         1010
  Q   K   G   F   V   P   F   L   V   S   A   T   A   G   T   T   V   Y   G   A
```

Figure 3B

```
ACAGAAAGGGTTTGTTCCTTTCCTCGTGAGTGCCACAGCTGGAACCACCGTGTACGGAGC
                    1030                      1050                      1070
 F  D  P  L  L  A  V  A  D  I  C  K  K  Y  K  I  W  M  H  V
ATTTGACCCCCTCTTAGCTGTCGCTGACATTTGCAAAAAGTATAAGATCTGGATGCATGT
                    1090                      1110                      1130
 D  A  A  W  G  G  G  L  L  M  S  R  K  H  K  W  K  L  S  G
GGATGCAGCTTGGGGTGGGGGATTACTATGTCCCGAAAACACAAGTGAAACTGAGTGG
                    1150                      1170                      1190
 V  E  R  A  N  S  V  T  W  N  P  H  K  M  M  G  V  P  L  Q
CGTGGAGAGGGCCAACTCTGTGACGTGGAATCCACACAAGATGATGGGAGTCCCTTTGCA
                    1210                      1230                      1250
 C  S  A  L  V  R  E  E  G  L  M  Q  N  C  N  Q  M  H  A
GTGCTCTGCTCTCCTGGTTAGAGAGGATTGATGCAGAATTGCAACCAAATGCATGC
                    1270                      1290                      1310
 S  Y  L  F  Q  Q  D  K  H  Y  D  L  S  Y  D  T  G  D  K  A
CTCCTACCTCTTTCAGCAAGATAAACATTATGACCTGTCCTATGACACTGGAGACAAGGC
                    1330                      1350                      1370
 L  Q  C  G  R  H  V  D  V  F  K  L  W  L  M  W  R  A  K  G
CTTACAGTGCGGACGCCACGTTGATGTTTTAAACTATGGCTGATGTGGAGGCAAAGGG
                    1390                      1410                      1430
 T  T  G  F  F  E  A  H  V  D  K  C  L  E  L  A  E  Y  L  Y  N
GACTACCGGGTTTGAAGCGCATGTTGATAAATGTTTGGAGTTGGCAGAGTATTATACAA
                    1450                      1470                      1490
 I  I  K  N  R  E  G  Y  E  M  V  F  D  G  K  P  Q  H  T  N
CATCATAAAAAACCGAGAAGGATATGAGATGGTGTTTGATGGGAAGCCTCAGCACACAAA
                    1510                      1530                      1550
```

Figure 3C

```
V   C   F   W   Y   I   P   P   S   L   R   T   L   E   D   N   E   E   R   M
TGTCTGCTTCTGGTACATTCCTCCAAGCTTGCGTACTCTGGAAGACAATGAAGAGAGAAT
         1570                 1590                1610

S   R   L   S   K   V   A   P   V   I   K   A   R   M   M   E   Y   G   T   T
GAGTCGCCTCTCGAAGGTGGCTCCAGTGATTAAAGCCAGAATGATGGAGTATGGAACCAC
         1630                 1650                1670

M   V   S   Y   Q   P   L   G   D   K   V   N   F   F   R   M   V   I   S   N
AATGGTCAGCTACCAACCCTTGGGAGACAAGGTCAATTCTTCCGCATGGTCATCTCAAA
         1690                 1710                1730

P   A   T   H   Q   D   I   D   F   L   I   E   E   I   E   R   L   G   Q
CCCAGCGCAACTCACCAAGACATTGACTTCCTGATTGAAGAATAGAACGCCTTGGACA
         1750                 1770                1790

D   L   *
AGATTTATAATAACCCTGCTCACCAAGCTGTTCCACTTCTCCTAGGTAGACAATTAAGTTG
         1810                 1830                1850

TCACAAACTGTGTGAATGTATTTGTAGTTTGTTCCAAAGTAAATCTATTTCTATATTGTG
         1870                 1890                1910

GTGTCAAAGTAGAGTTTAAAAATTAAACAAAAAGACATTGCTCCTTTAAAAGTCCTTT
         1930                 1950                1970

CTTAAGTTTAGAATACCTCTCTAAGAATTCGTGACAAAGGCTATGTTCTAATCAATAAG
         1990                 2010                2030

GAAAAGCTTAAAATTGTTATAAATACTTCCCTTACTTTTAATATAGTGTGCAAAGCAAAC
         2050                 2070                2090
```

Figure 3D

GAP WEIGHT: 3.000    LENGTH WEIGHT: 0.100    QUALITY: 856.2    RATIO: 1.464
PERCENT SIMILARITY: 97.436    4817, PEP    HGT2.PEP    AVERAGE MATCH: 0.540
AVERAGE MISMATCH: -0.396    LENGTH: 585    GAPS: 0    PERCENT IDENTITY: 96.068
AUGUST 22, 1990 08:20 **

```
  1 MASPGSGFWSFGSEDGSGDPENPGTARAWCQVAQKFTGGIGNKLCALLYG   50
    |||||||||||||||||||.||||||||||||||||||||||||||||||
  1 MASPGSGFWSFGSEDGSGDSENPGTARAWCQVAQKFTGGIGNKLCALLYG   50

51 DSEKPAESGGSVTSRAATRKVACTCDQKPCSCPKGDVNYALLHATDLLPA  100
    |.|||||||| ..||.|.|||.|..|||||.|.||||||.|||||||||
 51 DAEKPAESGGSQPPRAAARKAACACDQKPCSCSKVDVNYAFLHATDLLPA  100

101 CEGERPTLAFLQDVMNILLQYVVKSFDRSTKVIDFHYPNELLQEYNWELA  150
    |.||||||||||||||||||||||||||||||||||||||||||||||||
101 CDGERPTLAFLQDVMNILLQYVVKSFDRSTKVIDFHYPNELLQEYNWELA  150

151 DQPQNLEEILTHCQTTLKYAIKTGHPRYFNQLSTGLDMVGLAADWLTSTA  200
    ||||||||||.|||||||||||||||||||||||||||||||||||||||
151 DQPQNLEEILMHCQTTLKYAIKTGHPRYFNQLSTGLDMVGLAADWLTSTA  200

201 NTNMFTYEIAPVFVLLEYVTLKKMREIIGWPGGSGDGIFSPGGAISNMYA  250
    ||||||||||||||||||||||||||||||||||||||||||||||||||
201 NTNMFTYEIAPVFVLLEYVTLKKMREIIGWPGGSGDGIFSPGGAISNMYA  250
```

Figure 4A

```
251  MLIARYKMFPEVKEKGMAAVPRLIAFTSEHSHFSLKKGAAALGIGTDSVI  300
     ||: ||:||||||||||||: ||||||||||||||||||||| |||||||
251  MMIARFKMFPEVKEKGMAALPRLIAFTSEHSHFSLKKGAAALGIGTDSVI  300

301  LIKCDERGKMIPSDLERRILEVKQKGFVPFLVSATAGTTVYGAFDPLLAV  350
     ||||||||||||||||||||| |||||||||||||||||||||||||||
301  LIKCDERGKMIPSDLERRILEAKQKGFVPFLVSATAGTTVYGAFDPLLAV  350

351  ADICKKYKIWMHVDAAWGGGLLMSRKHKWKLNGVERANSVTWNPHKMMGV  400
     |||||||||||||||||||||||||||||||.|||||||||||||||||
351  ADICKKYKIWMHVDAAWGGGLLMSRKHKWKLSGVERANSVTWNPHKMMGV  400

401  PLQCSALLVREEGLMQSCNQMHASYLFQQDKHYDLSYDTGDKALQCGRHV  450
     ||||||||||||||| |||||||||||||||||||||||||||||||||
401  PLQCSALLVREEGLMQNCNQMHASYLFQQDKHYDLSYDTGDKALQCGRHV  450

451  DVFKLWLMWRAKGTTGFEAHIDKCLELAEYLYNIIKNREGYEMVFDGKPQ  500
     |||||||||||||||||||:||||||||||||||||||||||||||||||
451  DVFKLWLMWRAKGTTGFEAHVDKCLELAEYLYNIIKNREGYEMVFDGKPQ  500

501  HTNVCFWFVPPSLRVLEDNEERMSRLSKVAPVIKARMMEYGTTMVSYQPL  550
     ||||||||:|||||.|||||||||||||||||||||||||||||||||||
501  HTNVCFWYIPPSLRTLEDNEERMSRLSKVAPVIKARMMEYGTTMVSYQPL  550

551  GDKVNFFRMVISNPAATHQDIDFLIEEIERLGQDL  585
     ||||||||||||||||||||||||||||||||||
551  GDKVNFFRMVISNPAATHQDIDFLIEEIERLGQDL  585
```

Figure 4B

NUCLEIC ACID ENCODING GAD65

CROSS-REFERENCE TO RELATED APPLICATION

This application is a continuation of U.S. patent application Ser. No. 07/586,536, filed Sep. 21, 1990, now U.S. Pat. No. 6,682,906.

The present invention was supported by Grant NS22256 from the National Institutes of Health. The United States Government has certain rights in this invention.

BACKGROUND OF THE INVENTION

1. Field of the Invention

The present invention relates to the use of recombinant DNA technology for the transformation of a host organism with glutamic acid decarboxylase$_{65}$ (GAD$_{65}$) for the expression of GAD$_{65}$ polypeptides. Also encompassed are methods of using GAD$_{65}$ polypeptides diagnostically and therapeutically in autoimmune disease.

2. Description of the Background Art

Insulin-dependent diabetes mellitus (IDDM; type I diabetes) is one of the most common metabolic disorders. In the United States, IDDM affects approximately one in 300 to 400 people, and epidemiological studies suggest that its incidence is increasing. The disease results from the autoimmune destruction of the insulin-producing β-cells of the pancreas. More specifically, the preonset stage is characterized by "insulitis", in which lymphocytes infiltrate the pancreatic islets and selectively destroy the β-cells. The typical IDDM presentation of hyperglycemia appears only after at least 80% of the insulin-producing β-cells are lost. The remaining β-cells are destroyed during the next few years.

Although insulin therapy allows most IDDM patients to lead normal lives, this replacement is imperfect and does not completely restore metabolic homeostasis. Thus, severe complications which result in dysfunctions of the eye, kidney, heart, and other organs are common in IDDM patients undergoing insulin therapy. Because of this, it is highly desirable to extend the latency period (e.g., through administration of immunosuppressant drugs) between the start of β-cell destruction and the actual requirement of insulin replacement (i.e., when 80% of the β-cells are destroyed). Therefore, a diagnostic test which determines the beginning of β-cell destruction would allow the clinician to administer immunosuppressant drugs (Silverstein, et al., *New England Journal of Medicine*, 319: 599-604, 1988) to extend this latency period and thus significantly delay the onset of insulin replacement side effects.

Many IDDM patients have sera which contain antibodies to a 64 kD molecule (Baekkeskov, et al., *J. Clin. Invest,* 79:926-934, 1987; Atkinson, et al., *Lancet,* 335:1357-1360, 1990), to islet cell cytoplasmic (ICA) molecules or islet cell surface (ICSA) molecules (Bottazzo, et al, *Lancet,* 1:668-672, 1980), or to insulin (Palmer, et al., *Science,* 222:1137-1139, 1983; Atkinson, et al., *Diabetes,* 35:894-898, 1986). Atkinson and coworkers (Atkinson, et al., *Lancet,* 335:1357-1360, 1990) have demonstrated that the presence of antibodies to the 64 kD molecule in human sera appears to be the earliest and most reliable indicator that onset of IDDM symptoms will eventually occur.

Recently, Baekkeskov and coworkers established that the 64 kD molecule and glutamic acid decarboxylase (GAD) have several antigenic epitopes in common and thus they may be identical or very similar molecules. Although this identification is an important finding, the use of this information as a diagnostic tool for predicting IDDM is quite cumbersome and limited unless knowledge of the molecular biology of GAD is known. Consequently, the cloning and subsequent production of large quantities of the 64 kD molecule, or a GAD molecule which is antigenically substantially identical to the 64 kD molecule, will allow the development of a diagnostic kit designed to predict IDDM. The present invention provides a means for accomplishing this result.

SUMMARY OF THE INVENTION

The present invention arose out of the discovery that recombinant DNA technology could be used to produce eukaryotic GAD$_{65}$ polypeptide and that GAD$_{65}$ polypeptide could be used in the diagnosis and therapy of patients with autoimmune disease. Particularly relevant is the use of cloned eukaryotic GAD$_{65}$ polypeptide in the diagnosis of patients having, or at risk of having, insulin-dependent diabetes mellitus (IDDM).

A major advantage of the present invention is that it provides the art with a ready source of eukaryotic GAD$_{65}$ polypeptide corresponding to that purified from natural sources, while avoiding the problems associated with the isolation of naturally occurring eukaryotic GAD$_{65}$ polypeptide when separating it from other eukaryotic non-GAD$_{65}$ polypeptides. This absence of other eukaryotic non-GAD$_{65}$ polypeptides is significant in that it allows the development of test systems which will only detect antibodies specifically reactive with GAD$_{65}$ polypeptides.

Another advantage of providing eukaryotic GAD$_{65}$ polypeptide in host cells is that by so doing, it is possible to obtain much larger quantities of the polypeptide than are currently practicably available from natural sources. As a consequence, not only is it possible to use the polypeptide of the invention to more accurately classify patients with such autoimmune diseases as IDDM, but it is also now possible to provide commercially useful quantities of GAD$_{65}$ polypeptide for use in diagnostic systems.

DESCRIPTION OF THE DRAWINGS

FIGS. 2A-2D DNA sequence and corresponding amino acid sequence for rat GAD$_{65}$. SEQ ID NO:3 is the entire nucleotide sequence found in FIGS. 2A-2D. SEQ ID NO:4 is the nucleotide sequence for the coding region of FIGS. 2A-2D. SEQ ID NO:5 is the amino acid sequence of FIGS. 2A-2D.

FIGS. 3A-3D DNA sequence and corresponding amino acid sequence for human GAD$_{65}$. SEQ ID NO:6 is the entire nucleotide sequence found in FIGS. 3A-3D. SEQ ID NO:7 is the nucleotide sequence for the coding region of FIGS. 3A-3D. SEQ ID NO:8 is the amino acid sequence of FIGS. 3A-3D.

FIGS. 4A-4B Comparison to rat GAD$_{65}$ and human GAD$_{65}$ amino acid sequences.

DETAILED DESCRIPTION OF THE INVENTION

Figure 1:
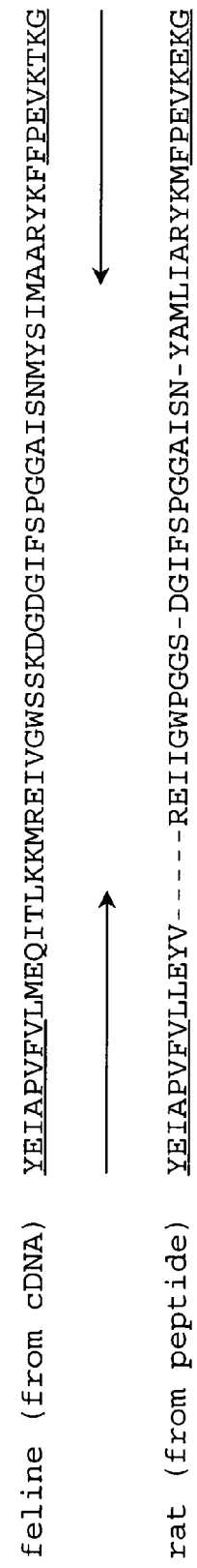
FIG. 1 Cloning strategy for obtaining GAD$_{65}$ and GAD$_{67}$ specific cDNA probes. The feline amino acid sequence of FIG. 1 is SEQ ID NO:1; the rat amino acid sequence of FIG. 1 is SEQ ID NO:2.

The present invention relates to the manipulation of genetic materials by recombinant procedures which make possible the production of polypeptides possessing part or all of the primary structural conformation for one or more of the epitopes for binding autoantibodies to glutamic acid decarboxylase$_{65}$ ($GAD_{65}$). These polypeptides are highly useful for the immunological detection of autoantibodies reactive with them, since such autoantibodies are indicative of autoimmune diseases such as insulin dependent diabetes mellitus and "stiff man" syndrome. These polypeptides can also be used for purposes of screening drugs, such as those that alter GAD function, and for generation of polyclonal and monoclonal antibodies which, in turn, can be used diagnostically to detect $GAD_{65}$.

The development of specific DNA sequences encoding eukaryotic $GAD_{65}$ polypeptide for splicing into DNA vectors can be accomplished using a variety of techniques. For example, alternative methods which can be employed include (1) the isolation of a double stranded DNA sequence from the genomic DNA of the eukaryote; (2) the chemical manufacture of a DNA sequence to provide the necessary codons for the polypeptide of interest; and (3) the in vitro synthesis of a double stranded DNA sequence by reverse transcription of mRNA isolated from a eukaryotic donor cell. In the latter case, a double stranded DNA complement of mRNA is eventually formed which is generally referred to as cDNA.

The manufacture of DNA sequences is frequently the method of choice when the entire sequence of amino acid residues of the desired polypeptide product is known. When the entire sequence of amino acid residues of the desired polypeptide is not known, the direct manufacture of DNA sequences is not possible and the method of choice is the formation of cDNA sequences. Among the standard procedures for isolating cDNA sequences of interest is the formation of plasmid-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double stranded DNA or RNA probe sequences duplicating a sequence putatively present in the target cDNA may be employed in DNA/DNA hybridization procedures which are carried out on cloned copies of the cDNA which have been denatured into a single stranded form (Jay, et al., *Nucleic Acid Research*, 11:2325, 1983).

Hybridization procedures are useful for the screening of recombinant clones by using labeled mixed synthetic oligonucleotide probes wherein each is potentially the complete complement of a specific DNA sequence in the hybridization sample which includes a heterogeneous mixture of denatured double stranded DNA. For such screening, hybridization is preferably performed on either single stranded DNA or denatured double stranded DNA. These procedures are particularly useful in the detection of cDNA clones derived from sources where an extremely low amount of mRNA sequences relating to the polypeptide of interest are present. In other words, by using stringent hybridization conditions directed toward avoidance of non-specific binding, it is possible, for example, to allow the autoradiographic visualization of a specific cDNA clone by the hybridization of the target DNA to that single probe in the mixture which is its complete complement (Wallace, et al., *Nucleic Acid Research*, 9:879, 1981).

In addition, a GAD cDNA library can be screened by injecting the various cDNAs into oocytes, allowing sufficient time for expression of the cDNA gene products to occur, and testing for the presence of the desired cDNA expression product, for example, by using antibody specific for $GAD_{65}$ polypeptide or by using functional assays for $GAD_{65}$ enzymatic activity.

Alternatively, a cDNA library can be screened indirectly for $GAD_{65}$ peptides having at least one epitope using antibodies to $GAD_{65}$ (Chang and Gottlieb, *J. Neurosci.*, 8:2123, 1988). Such antibodies can be either polyclonally or monoclonally derived and used to detect expression product indicative of the presence of $GAD_{65}$ cDNA. Preferred are antibodies directed to an epitope found in the first 100 amino acids of the N-terminal portion of $GAD_{65}$.

Of the three above-noted methods for developing specific DNA sequences for use in recombinant procedures, the use of genomic DNA isolates, is the least common This is especially true when it is desirable to obtain the microbial expression of mammalian polypeptides because of the presence of introns.

The present invention provides novel polypeptides of $GAD_{65}$ which have part or all of the primary structural conformation, that is, a continuous sequence of amino acid residues, having at least one epitope for antibodies to $GAD_{65}$.

It is possible to use the polypeptide fragments of the invention rather than intact $GAD_{65}$ to detect autoantibodies to $GAD_{65}$. The term "polypeptide," as applied to $GAD_{65}$ polypeptide, denotes any sequence of amino acids having an epitope for autoantibodies to $GAD_{65}$, wherein the sequence of amino acids is encoded by all or part of the cDNA sequences of the invention.

The polypeptides resulting from microbial expression of the DNA sequences of the invention can be further characterized by their freedom from association with other eukaryotic polypeptides or other contaminants which might otherwise be associated with $GAD_{65}$ in its natural cellular environment or in such extracellular fluids as plasma or urine.

Studies by the present inventors unequivocally establish that $GAD_{65}$ and $GAD_{67}$ are encoded by distinct genes and are not produced, for example, by post-transcriptional or post-translational modification of a common genomic sequence. Evidence proving that $GAD_{65}$ and $GAD_{67}$ are encoded by different genes include: (a) the largest contiguous sequence of exact identity between $GAD_{65}$ and $GAD_{67}$ cDNAs is only 17 nucleotides in length, (b) cDNAs from $GAD_{65}$ and $GAD_{67}$ do not cross hybridize with each other's or with each other's mRNA under low stringency conditions (2.0×SSC, 0.01% SDS, 23° C.), and (c) $GAD_{65}$ and $GAD_{67}$ cDNAs do not cross hybridize with isolated genomic clones encoding $GAD_{67}$ and $GAD_{65}$, respectively.

The term "host" is meant to include not only prokaryotes, but also such eukaryotes as yeast, filamentous fungi, as well as plant and animal cells which can replicate and express an intron-free DNA sequence of eukaryotic $GAD_{65}$. However, prokaryotes are preferred as the host organism.

The term "prokaryotes" is meant to include all bacteria which can be transformed or transfected with the gene for the expression of $GAD_{65}$. Prokaryotic hosts may include gram negative as well as gram positive bacteria such as, for example, *E. coli, S. typhimurium, Serratia marcescens* and *Bacillus subtilis*.

A recombinant DNA molecule coding for the $GAD_{65}$ polypeptides can be used to transform or transfect the host using any of the techniques commonly known to those of ordinary skill in the art. Especially preferred is the use of a plasmid or a virus containing the $GAD_{65}$ coding sequence for purposes of prokaryotic transformation or transfection, respectively.

Methods for preparing fused, operably linked genes and expressing them in bacteria are well-known in the art (Maniatis, et al., *Molecular Cloning: A Laboratory Manual*, Cold Spring Harbor Laboratory, Cold Spring Harbor, N.Y., 1989). The genetic constructs and methods described therein can be utilized for expression of $GAD_{65}$ in prokaryotic hosts.

In general, expression vectors containing promotor sequences which facilitate the efficient transcription of the inserted eukaryotic genetic sequence are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The polypeptides of the invention can then be isolated from the grown medium, cellular lysates, or cellular membrane fractions.

The isolation and purification of the microbially expressed polypeptides of the invention may be by any conventional means such as, for example, preparative chromatographic separations and immunological separations such as those involving the use of monoclonal or polyclonal antibody.

By having provided the sequence of amino acid residues of $GAD_{65}$, the present invention provides for the manufacture of DNA sequences which code for the host expression of polypeptide analogs or derivatives of $GAD_{65}$ which differ from naturally-occurring forms in terms of the identity or location of one or more amino acid residues and which share some or all of the epitopes of naturally-occurring polypeptide forms.

The novel DNA sequences of the invention include all sequences useful in providing the expression in prokaryotic or eukaryotic host cells of polypeptides which have at least a part of the primary structural conformation for one or more epitopes capable of reacting with autoantibodies to $GAD_{65}$ which are comprehended by: (a) the DNA sequence as set forth in FIGS. 2A-2D or 3A-3D or their complementary strands; (b) DNA sequences which hybridize to DNA sequences defined in (a) or fragments thereof; and (c) DNA sequences which, but for the degeneracy of the genetic code, would hybridize to DNA sequences defined in (a) and (b) above. Specifically comprehended in (b) are genomic DNA sequences which encode allelic variant forms of $GAD_{65}$. Part (c) specifically comprehends the manufacture of DNA sequences which encode $GAD_{65}$, and $GAD_{65}$ fragments, and $GAD_{65}$ analogs wherein the DNA sequences thereof may incorporate codons which facilitate translation of mRNA in non-vertebrate hosts.

Since the cDNA sequence of the invention encodes essentially the entire human or rat $GAD_{65}$ molecule, it is now a matter of routine to prepare, subclone, and express smaller polypeptide fragments of cDNA from this or a corresponding cDNA sequence which would encode as few as one epitope for autoantibodies to human or rat $GAD_{65}$. The presence of such an epitope on a cloned polypeptide can then be confirmed using, for example, sera from a patient with autoantibodies to $GAD_{65}$. An example of such a smaller peptide is the first approximately 100 amino acids from the N-terminus of $GAD_{65}$ (shown in FIGS. 3A-3D). This amino acid sequence is essentially absent from $GAD_{67}$.

The $GAD_{65}$ of the invention is particularly suited for use in immunoassays in which it can be utilized in liquid phase or bound to a solid phase carrier. In addition, $GAD_{65}$ used in these assays can be detectably labeled in various ways.

Examples of immunoassays which can utilize the $GAD_{65}$ of the invention are competitive and non-competitive immunoassays in either a direct or indirect format. Examples of such immunoassays are the radioimmunoassay (RIA), the sandwich (immunometric assay) and the Western blot assay. Detection of antibodies which bind to the $GAD_{65}$ of the invention can be done utilizing immunoassays which run in either the forward, reverse, or simultaneous modes, including immunohistochemical assays on physiological samples. The concentration of $GAD_{65}$ which is used will vary depending on the type of immunoassay and nature of the detectable label which is used. However, regardless of the type of immunoassay which is used, the concentration of $GAD_{65}$ utilized can be readily determined by one of ordinary skill in the art using routine experimentation.

The $GAD_{65}$ of the invention can be bound to many different carriers and used to detect the presence of antibody specifically reactive with the polypeptide. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding $GAD_{65}$, or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

Alternatively, the polypeptide of the invention can be used to detect antibodies to $GAD_{65}$ by measuring GAD enzymatic activity. For example, $GAD_{65}$ and a specimen suspected of having antibodies to $GAD_{65}$ can be incubated for a period of time and under conditions sufficient to allow binding to occur between $GAD_{65}$ and the antibodies. The reaction product is precipitated and then tested for GAD enzymatic activity.

For purposes of the invention, the antibody which binds to $GAD_{65}$ of the invention may be present in various biological fluids and tissues. Any sample containing a detectable amount of antibodies to $GAD_{65}$ can be used. Normally, a sample is a liquid such as urine, saliva, cerebrospinal fluid, blood, serum and the like, or a solid or semi-solid such as tissue, feces and the like.

The materials for use in the assay of the invention are ideally suited for the preparation of a kit. Such a kit may comprise a carrier means being compartmentalized to receive in close confinement one or more container means such as vials, tubes and the like, each of the container means comprising one of the separate elements to be used in the method. For example, one of the container means may comprise $GAD_{65}$ bound to a carrier. A second container may comprise soluble, detectably-labeled second antibody, in lyophilized form or in solution.

In addition, the carrier means may also contain a plurality of containers each of which comprises different, predetermined amounts of $GAD_{65}$. These latter containers can then be used to prepare a standard curve into which can be interpolated the results obtained from the sample containing the unknown amount of autoantibodies to $GAD_{65}$.

In using the kit all the user has to do is add, to a container, a premeasured amount of a sample containing a measurable, yet unknown amount of autoantibodies to $GAD_{65}$ to be detected, a premeasured amount of carrier-bound $GAD_{65}$ present in the first container, and a premeasured amount of the detectably labeled second antibody present in the second container. Alternatively, the non-detectably labeled $GAD_{65}$ can be provided attached to the container to which the sample and the detectably labeled second antibody are added. After an appropriate time for incubation, an immune complex is formed and is separated from the supernatant fluid, and the immune complex or the supernatant fluid are detected, as by radioactive counting or addition of an enzyme substrate, and color development.

The term "ameliorate" denotes a lessening of the detrimental effect of the autoimmune response in the patient receiving therapy. The term "therapeutically effective" means that the amount of $GAD_{65}$ polypeptide used is of sufficient quantity to ameliorate the cause of disease due to the autoimmune response.

The recombinant $GAD_{65}$ polypeptides of the invention can also be used therapeutically in patients having an autoimmune response to $GAD_{65}$. Such therapy can be accomplished by, for example, the administration of recombinant $GAD_{65}$ polypeptide. Such administration can utilize unlabeled as well as labeled $GAD_{65}$ polypeptide. When unlabeled $GAD_{65}$ polypeptide is utilized advantageously, it would be in a form wherein, for example, the $GAD_{65}$ polypeptides are in fragments which are too small to stimulate an immune response, but large enough to bind, or block, the continuance of the autoimmune response. For example, $GAD_{65}$ could be digested enzymatically into epitope-sized peptides (typically 5-12 amino acids in length) and thereby bind to Fab binding portions present in the body fluids, or on the surface of immune cells, of the patient with autoimmune disease.

Alternatively, the recombinant $GAD_{65}$ polypeptides of the invention could be administered labeled with a therapeutic agent. These agents can be coupled either directly or indirectly to the $GAD_{65}$ polypeptides of the invention. One example of indirect coupling is by use of a spacer moiety. These spacer moieties, in turn, can be either insoluble or soluble (Diener, et al., Science, 231:148, 1986) and can be selected to enable drug release from the $GAD_{65}$ polypeptide at the target site. Examples of therapeutic agents which can be coupled to the $GAD_{65}$ polypeptides of the invention for immunotherapy are drugs, radioisotopes, lectins, and toxins.

The drugs with which can be conjugated to the $GAD_{65}$ polypeptides of the invention include compounds which are classically referred to as drugs such as mitomycin C, daunorubicin, and vinblastine.

In using radioisotopically conjugated $GAD_{65}$ polypeptides of the invention for immunotherapy, certain isotopes may be more preferable than others depending on such factors as leukocyte distribution as well as stability and emission. Depending on the autoimmune response, some emitters may be preferable to others. In general, α and β particle-emitting radioisotopes are preferred in immunotherapy. Preferred are short range, high energy α emitters such as $^{212}Bi$. Examples of radioisotopes which can be bound to the $GAD_{65}$ polypeptides of the invention for therapeutic purposes are $^{125}I$, $^{131}I$, $^{90}Y$, $^{67}Cu$, $^{212}Bi$, $^{211}At$, $^{212}Pb$, $^{47}Sc$, $^{109}Pd$ and $^{188}Re$.

Lectins are proteins, usually isolated from plant material, which bind to specific sugar moieties. Many lectins are also able to agglutinate cells and stimulate lymphocytes. However, ricin is a toxic lectin which has been used immunotherapeutically. This is accomplished by binding the α-peptide chain of ricin, which is responsible for toxicity, to the antibody molecule to enable site specific delivery of the toxic effect.

Toxins are poisonous substances produced by plants, animals, or microorganisms that, in sufficient dose, are often lethal. Diphtheria toxin is a substance produced by *Corynebacterium diphtheria* which can be used therapeutically. This toxin consists of an α and β subunit which under proper conditions can be separated. The toxic A component can be bound to $GAD_{65}$ polypeptide and used for site specific delivery to a leukocyte expressing a receptor for $GAD_{65}$ polypeptide. Other therapeutic agents which can be coupled to the $GAD_{65}$ polypeptides of the invention, as well as ex vivo and in vivo therapeutic protocols, are known, or can be easily ascertained, by those of ordinary skill in the art.

The dosage ranges for the administration of the $GAD_{65}$ polypeptides of the invention are those large enough to produce the desired effect in which the symptoms or cellular destruction of the autoimmune response are ameliorated. The dosage should not be so large as to cause adverse side effects, such as unwanted cross-reactions, anaphylactic reactions, and the like. Generally, the dosage will vary with the age, condition, sex, and extent of the disease in the patient and can be determined by one of skill in the art. The dosage can be adjusted by the individual physician in the event of any counterindications. Dosage can vary from about 0.1 mg/m² to about 2000 mg/m², preferably about 0.1 mg/m² to about 500 mg/m²/dose, in one or more dose administrations daily, for one or several days.

The $GAD_{65}$ polypeptides of the invention can be administered parenterally by injection or by gradual perfusion over time. The $GAD_{65}$ polypeptides of the invention can be administered intravenously, intraperitoneally, intra-muscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also relates to a method for preparing a medicament or pharmaceutical composition comprising the $GAD_{65}$ polypeptides of the invention, the medicament being used for therapy of autoimmune response to $GAD_{65}$.

The above disclosure generally describes the present invention. A more complete understanding can be obtained by reference to the following specific examples which are provided herein for purposes of illustration only and are not intended to limit the scope of the invention.

EXAMPLE 1

Cloning and Expression of $GAD_{65}$

A. Recombinant DNA Procedures

In order to obtain cDNA probes specific for $GAD_{65}$ and $GAD_{67}$, total RNA was extracted from adult rat brain by guanidine isothiocyanate-cesium gradient using the method of Chirgwin, et al. (*Biochemistry*, 18:5294, 1979). Poly (A) RNA was purified on oligo dT cellulose, using the protocol by Bethesda Research Laboratories (BRL). First strand synthesis was performed by using MMLV-reverse transcriptase (BRL), with conditions suggested, except that poly $d(N_6$-mers (Pharmacia) were used as primers. This cDNA-RNA mixture was heat inactivated at 65° C. for 15 min and stored at −20° C. For PCR, 1/50 of the sample was added to the 100 μl reaction. Degenerate oligonucleotides were synthesized (Applied Biosystems) to encode the underlined common amino acid sequences of feline (from cDNA) (Kobayashi, et al., *J. Neurosci.*, 7:2768, 1987) and rat (from peptides) (Chang and Gottlieb, *J. Neurosci.*, 8:2123, 1988) GAD (FIG. 1). The 5'-end sequence of each degenerate oligonucleotide contained one strand of the DNA sequence recognized by either SstI and HindIII (5' oligo) or SstI and SstII (3'-end oligo). These primers were used for selective amplification by polymerase chain reaction of the generated cDNA template as described by Gould, et al., (*Proc. Natl. Acad. Sci., USA*, 86:1934, 1989). PCR products were subcloned into HindIII/SstI double digested Bluescript SK vector (Stratagene), transformed into DH5 (BRL), and plated by standard methods (Maniatis, et al., *Molecular Cloning: A Laboratory Manual*, Cold Spring Harbor Laboratory, Cold Spring Harbor, N.Y., 1989).

Colony hybridization was done with an $5'-{}^{32}P$ end labeled oligonucleotide specific to feline $GAD_{67}$ (Kobayashi, et al., *J. Neurosci.*, 7:2768, 1987). End labeling of oligonucleotide, hybridization conditions, and washing conditions were done as described (Wallace, et al., in *Guide to Molecular Cloning Techniques*; Berger, et al., Eds. in *Methods of Enzymology*; Abelson, et al., Eds. *Academic Press, Inc.*, San Diego, 432-442, 1987), except that the nitrocellulose filters were washed at 50° C. for 15 min. Colonies which were positive and negative in the hybridization were individually picked and grown overnight in Terrific Broth (Tartof, et al., *Focus*, 9:12, 1987). DNA was isolated using a boiling method (Maniatis, et al., *Molecular Cloning: A Laboratory Manual*, Cold Spring Harbor Laboratory, Cold Spring Harbor, N.Y., 1989) and templates were denatured by 0.2N NaOH and purified by Sephacryl S400 spun columns (Pharmacia). Sequencing of denatured double stranded template was by the chain-termination method (Sanger, et al., *Proc. Natl. Acad. Sci., USA*, 74:5463, 1977) using the T7-sequencing kit (Pharmacia).

As shown in FIG. 1, PCR-generated rat $GAD_{65}$ and $GAD_{67}$ cDNAs were used as probes to screen a lambda ZAP (Stratagene) rat hippocampus library provided by S. Heinemann (Salk Institute) by standard techniques (Maniatis, et al., *Molecular Cloning: A Laboratory Manual*, Cold Spring Harbor Laboratory, Cold Spring Harbor, N.Y., 1989). A 2400 nucleotide $GAD_{65}$ cDNA (the largest clone) was isolated and subcloned by "zapping" as described by Stratagene. When a rat $GAD_{67}$ cDNA was obtained which was smaller than a 3.2 kb rat $GAD_{67}$ cDNA clone already on hand, the larger cDNA was sequenced. Exo III deletions (Henikoff, *Gene*, 28:351, 1984) were made in both directions for $GAD_{65}$ and $GAD_{67}$ and templates were prepared and sequenced as described above. Anchored PCR (Frohman, et al., *Proc. Natl. Acad. Sci., USA*, 85:8998, 1988) was done to clone the remaining 5'-ends of $GAD_{65}$ and $GAD_{67}$ mRNAs which were not represented in the original cDNA clones isolated in the library screening. Sequencing of these clones revealed that neither $GAD_{65}$ nor $GAD_{67}$ mRNAs contained any further initiation codons (AUGs) in frame with the previously designated initiation codons of the original cDNA clones.

EXAMPLE 2

Characterization of Cloned $GAD_{65}$

A. Northern Blot Hybridization

Two PCR-derived cDNA probes were hybridized to Northern blots containing rat brain RNA in order to determine whether the $GAD_{67}$ and $GAD_{65}$ cDNAs were derived from two different mRNAs. RNA was extracted as described in Example 1. Poly (A) RNA was separated by electrophoresis in formaldehyde and transferred onto Biotrans (ICN) membranes, and hybridization was performed as described by Well, et al. (*J. Neurosci.*, 16:311, 1986), except that 100 μl/ml of poly (A) was added. Probes were labeled to approximately $10^9$ dpm/μg by the oligolabeling procedure of Feinberg and Vogelstein (*Anal. Biochem.*, 132:6, 1983). Identical results were subsequently obtained with full-length clones of $GAD_{65}$ and $GAD_{67}$ cDNAs.

Figure 5:
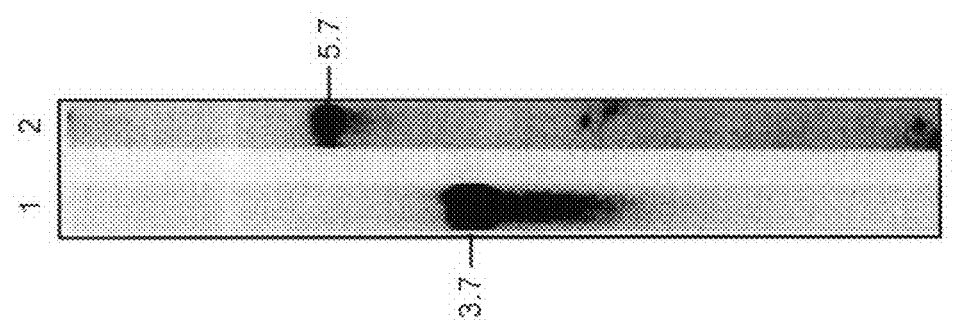
FIG. 5 GAD$_{65}$ and GAD$_{67}$ cDNAs hybridize to different size RNAs.

As shown in FIG. 5, lanes 1 and 2 contain 1 μg of poly (A) selected RNA extracted from rat cerebellum. Lane 1 was hybridized to a cDNA probe for the rat cognate of feline $GAD_{57}$ (Kobayashi, et al., *J. Neurosci.*, 7:2768, 1987) and lane 2 with a cDNA probe for the rat peptide sequence (which corresponds to $GAD_{65}$).

The cDNA probe for the rat peptide sequence hybridized to a 5.7 kb RNA, while the cDNA probe for the rat cognate of our feline cDNA, hybridized to a 3.7 kb RNA. This demonstrates that $GAD_{65}$ and $GAD_{67}$ are not derived from the same mRNA.

B. Genomic Hybridization of $GAD_{67}$ and $GAD_{65}$

In order to investigate the possibility that $GAD_{67}$ and $GAD_{65}$ arise from separate genes, cDNAs of both $GAD_{67}$ and $GAD_{65}$ were hybridized to DNA blots containing genomic DNA.

For Southern blots, genomic DNA was extracted from rat liver as described (Kaiser, et al., in *DNA Cloning*, vol. I, A Practical Approach, D. M. Glover ed., IRL Press, Oxford, 38-40, 1985). DNA (10 μg/sample) was digested to completion with EcoRI and HindIII using conditions recommended by the suppliers (BRL, Gaithersburg, Md.). DNA fragments were separated by electrophoresis at 1.5 v/cm for 16 hrs in 0.8% agarose. The DNA was then transferred to Zeta-Probe membranes (Bio-Rad), hybridized, and washed, as described by Gatti, et al. (*Biotechniques*, 2:148, 1984), except that 5 μg/ml Carnation dried milk was substituted for Denhardt's solution. Probes for Southern blots were labeled as described in Example 1, above.

Figure 6:
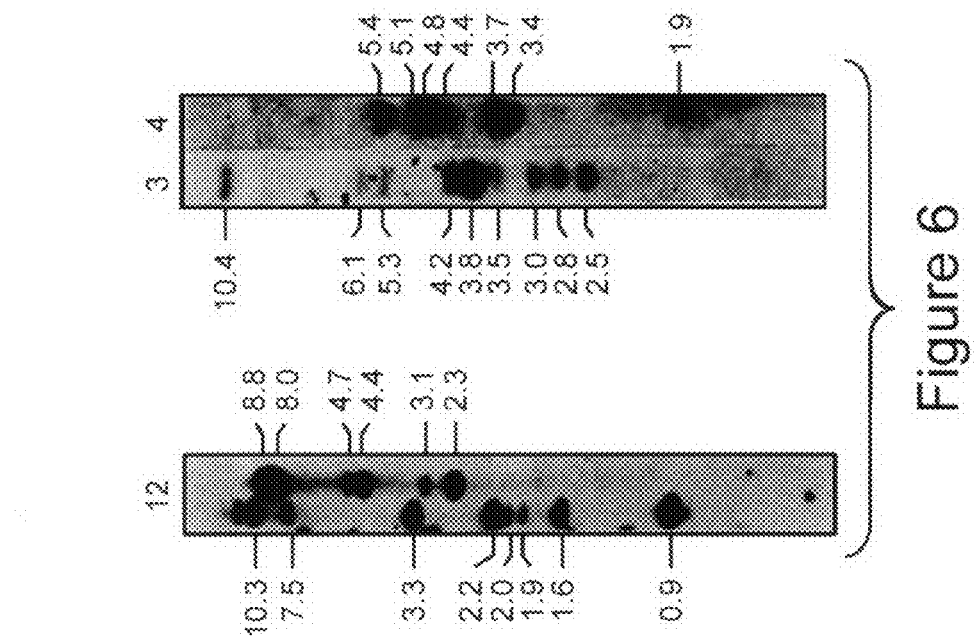
FIG. 6 Southern blots hybridized with cDNA probes specific for GAD$_{65}$ and GAD$_{67}$.

As shown in FIG. 6, genomic DNA digested with HindIII and EcoRI are in lanes 1 and 3 and lanes 2 and 4, respectively. $GAD_{67}$ cDNA was hybridized to lanes 1 and 2, whereas $GAD_{65}$ cDNA was hybridized to lanes 3 and 4. Numbers along the side of the gel are the DNA fragment sizes in kilobases.

This data shows that the two cDNAs hybridize to genomic fragments of different sizes. In addition, the greatest contiguous stretch of identical nucleotide sequence of $GAD_{65}$ and $GAD_{67}$ cDNAs is only 17 nucleotide bases in length. Thus, $GAD_{67}$ and $GAD_{65}$ are encoded by two distinct genes.

C. Enzymatic Comparison of $GAD_{67}$ and $GAD_{65}$

Studies were done comparing the effect of PLP on the activity of $GAD_{67}$ and $GAD_{65}$. In so doing, both cDNAs were subcloned into vectors that allowed their expression in bacteria (Studier, et al., *J. Mol. Biol*, 189:113, 1986). Overexpression of "fusionless" $GAD_{65}$ and $GAD_{67}$ was accomplished by subcloning $GAD_{65}$ cDNA into the NcoI site of pET-8c and $GAD_{67}$ cDNA into the NheI site of pET-5c vectors (Studier, et al., *J. Mol. Biol*, 189:113, 1986).

To obtain compatible sticky ends for correct in-frame subcloning of both cDNAs, selective amplification was performed by PCR using conditions suggested by United States Biochemical (USB), with 200 μM dNTPs and 1.5 mM $MgCl_2$ in the mixture and annealing at 55° C. with 20 cycles to decrease infidelity of AmpliTAQ (USB). Primers specific for $GAD_{65}$ and $GAD_{67}$ contained one DNA strand of the NcoI and SpeI recognition sites, respectively. Since there is a NheI restriction site within the coding region of $GAD_{67}$, SpeI (which is compatible with NheI) was used.

PCR products were subcloned into their respective pET vectors, transformed into DH5 and plated as described (Maniatis, et al., *Molecular Cloning: A Laboratory Manual*, Cold Spring Harbor Laboratory, Cold Spring Harbor, N.Y., 1989). Colonies were picked and grown overnight in LB broth with 50 μg/ml ampicillin. Subclones with correct orientation were transformed into BL21 (DE3) strain (Studier, et al., *J. Mol. Biol.*, 189:113, 1986) for overexpression. As a negative control, the pET-8C vector with no insert was transformed and subsequently induced. Single colonies were picked, grown, induced by 1 mM isopropyl-B-D-thiogalacto-pyranoside (IPTG), and analyzed on SDS-PAGE gels as described (Sambrook, et al., *Molecular Cloning a Laboratory Manual*, Cold Spring Harbor Laboratory Press, Cold Spring Harbor, 17.15-17.16, 1989).

To measure GAD activity, we induced 10 ml cultures of bacteria at $OD_{600}$-0.5 with 1 mM IPTG. Two hours after induction, bacteria was spun down and resuspended and sonicated in 1 ml of homogenizing buffer (1 mM phenylmethylsulfonyl fluoride (PMSF), 1 mM 2-aminoethylisothiouronium bromide (AET), and 60 mM potassium phosphate, pH 7.1). After sonication, cell debris was removed by centrifugation and protein concentration was measured (Bradford, *Anal. Biochem.*, 72:248, 1986) in the supernatant (supernatant was stored in aliquots at −70° C.). Brain homogenates were prepared as described (Legay, et al., *J. Neurochem.*, 46:1478, 1986). GAD activity was measured as described (Krieger, et al., *J. Neurochem.*, 33:299, 1984) with 0.2 mM PLP present or absent and 20 μl of brain homogenate or bacterial lysate in the incubation mixture. Production of $^{14}CO_2$ in bacterial lysates was linear with respect to time of incubation and protein concentration.

TABLE 1

| Source | GAD Specific Activity[a] | | Fold Increase in Induction |
|---|---|---|---|
| | −PLP | +PLP | |
| BL21(DE3) + pET-8c | 12 ± 0.4 | 9 ± 1 | — |
| BL21(DE3) + pET-$GAD_{65}$ | 115 ± 3 | 773 ± 61 | 6.7 |
| BL21(DE3) + pET-$GAD_{67}$ | 160 ± 2 | 389 ± 8 | 2.4 |
| Rat Brain | 131 ± 5 | 216 ± 2 | 1.6 |

[a]cpms of $^{14}CO_2$/μg protein/hr of triplicates ± S.E.M.

As shown in Table 1, bacterial lysates containing $GAD_{65}$ or $GAD_{67}$ catalyze the conversion of [1-$^{14}$C]-glutamate to GABA and $^{14}CO_2$.

PLP stimulates the enzymatic activity of $GAD_{65}$ more than $GAD_{67}$. This greater stimulation probably reflects the faster cycling of $GAD_{65}$ through the inactivation cycle proposed by Martin and coworkers (Martin, *Cell. Mol. Neurobiol.*, 7:237, 1987). This faster cycling suggests that $GAD_{65}$ contributes more to the pool of apo-GAD that exists in vivo (Miller, et al., *Brain Res. Bull.*, 5(Suppl. 2):89, 1980). Thus, in vivo, PLP appears to regulate $GAD_{65}$ activity more than $GAD_{67}$ activity.

$GAD_{65}$ activity in bacterial lysates is similar to the fivefold PLP stimulation of GAD activity found in synaptosomes prepared from rat substantia nigra (Miller, et. al., *J. Neurochem.*, 33:533, 1979). Because both GADs are more dependent upon added PLP in bacteria than is the GAD activity in crude rat brain homogenates, the endogenous PLP concentration of bacteria lysates may be less than rat brain homogenates.

D. Immunological Identification of $GAD_{65}$ and $GAD_{67}$

Rat brain homogenates and bacterial lysates were extracted as described above. Equal volumes of loading buffer were added to each sample as described (Harlow, et al., *Antibodies, A Laboratory Manual*, Cold Spring Harbor Laboratory, Cold Spring Harbor, N.Y., 1988). Proteins were separated by electrophoresis in a 10% acrylamide gel in SDS and electrophoretically transferred to nitrocellulose (Harlow, et al., *Antibodies, A Laboratory Manual*, Cold Spring Harbor Laboratory, Cold Spring Harbor, N.Y., 1988). The unreacted sites were blocked with a phosphate buffered saline (PBS) solution containing 2% bovine serum albumin (fraction V), 1% gelatin, and 1% Triton-X-100 at 42° C. for one hr. After washing, the nitrocellulose filter was then cut into three sections and incubated with the following primary antibodies: lanes 1 to 4 with a 1/2000 dilution of the antiserum of Oertel, et al. (*Neuroscience*, 6:2689, 1981), which recognizes both $GAD_{67}$ and $GAD_{65}$; lanes 5-8 with a 1/2000 dilution of K-2 antiserum, which recognizes only $GAD_{67}$; lanes 9-12 with a 1/2000 dilution of GAD-6 monoclonal antibody, which is specific for $GAD_{65}$ (Chang, et al., *J. Neurosci.*, 8:2123, 1988). All filters were extensively washed and appropriate secondary antibodies were incubated and washed. Bound antibodies were detected with $^{125}$I-labeled protein A and autoradiography. Each lane contained the following: lanes 1, 5, and 9 are BL21 (DE3)+pET-$GAD_{67}$; lanes 2, 6, and 10 are BL21 (DE3)+pET-$GAD_{65}$; lanes 3, 7, and 11 are rat brain homogenate; and lanes 4, 8, and 12 are BL21 (DE3)+pET-8c.

Figure 7:
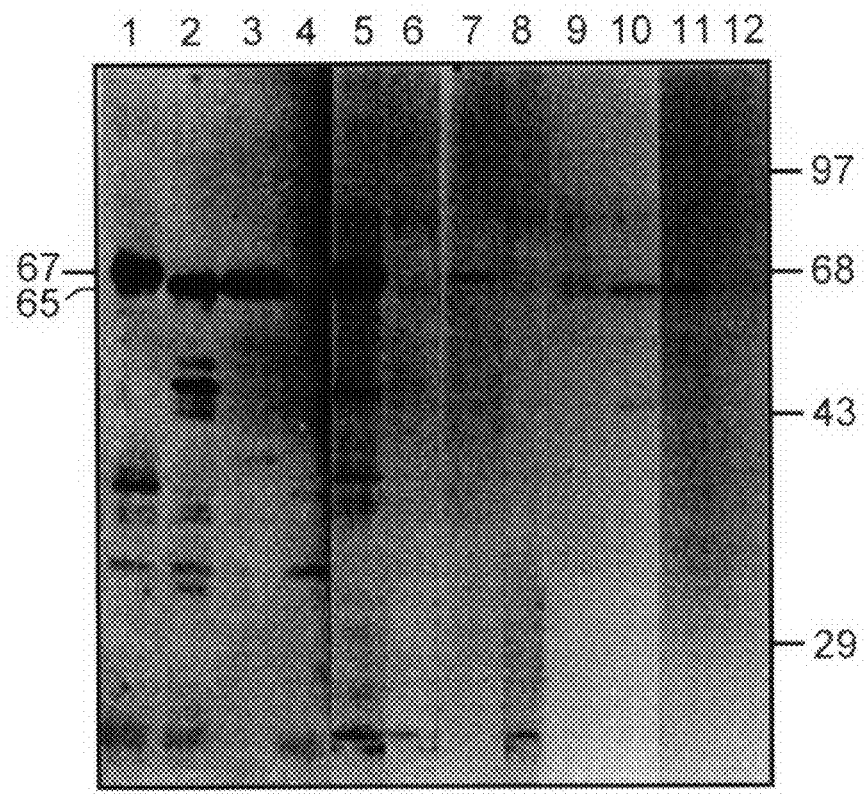
FIG. 7 Immunological identification of GAD$_{65}$ and GAD$_{67}$.

The immunoblots of bacterially produced $GAD_{65}$ and $GAD_{67}$ demonstrated that $GAD_{65}$ indeed corresponds to the smaller GAD in brain extracts, and $GAD_{67}$ to the larger form (FIG. 7). Previous work has demonstrated the correspondence of $GAD_{67}$ to the larger GAD for feline $GAD_{67}$, and for mouse $GAD_{67}$ (Katarova, et al., *Eur. J. Neurosci.*, 2:190, 1990; 235, 1987). The mobilities of bacterially produced $GAD_{65}$ and $GAD_{67}$ (as detected with the antiserum of Oertel, et al. (*Neuroscience*, 6:2689, 1981) are identical to the immunoreactive doublet seen in rat brain homogenate.

The smaller molecular weight and larger molecular weight forms of GAD in rat brain are thus identical in antigenicity and size to the products of $GAD_{65}$ and $GAD_{67}$ cDNAs, respectively. Consequently, the two GADs in rat brain are $GAD_{65}$ and $GAD_{67}$. From this data it can also be concluded that the molecular identity of the reported PLP-dependent and PLP-independent GADs by Tapia (Bayon, et al., *J. Neurochem.*, 29:519, 1977) are $GAD_{65}$ and $GAD_{67}$, respectively. Martin and coworkers (Spink, et al., *Brain Res.*, 421:235, 1987) have reported the existence of four kinetically different forms of rat brain GAD. However, immunoblotting experiments (with the antisera used here) of these forms have not been reported.

E. Distribution of $GAD_{65}$ and $GAD_{67}$ in RNAs in Brain Tissue

Experiments were done to determine the distribution of $GAD_{65}$ and $GAD_{67}$ in RNAs in cerebellum using in situ hybridization.

Transcripts of, respectively, 3.2 kb and 2.3 kb from $GAD_{65}$ and $GAD_{67}$ cDNAs, were radiolabeled with $^{35}S$ according to Wuenschell, et al. (*Proc. Natl. Acad. Sci., USA* 83:6193, 1986) procedure. Hydrolyzed fragments of 200 bp were hybridized to coronal sections of a rat cerebellum. Animals were anesthetized under halothane and decapitated. The brain was rapidly frozen in dry ice and coronal frozen sections (12 μm) were fixed for 30 min in freshly prepared 4% formaldehyde in phosphate-buffered saline (PBS; 130 mM NaCl, 10 mM Na phosphate, pH 7.0). The tissue was dehydrated through graded ethanol solutions and stored at −70° C.

In order to increase tissue permeability, the sections were submitted to the following pretreatments: rehydration through graded ethanol solutions (5 min each in 95%, 85%, 70%, 50%, and 30% ethanol); PBS (5 min); 0.02N HCl (10 min); PBS (5 min); 0.01% Triton N-101 in PBS (1 min); PBS (2×5 min); 1 μg/ml proteinase K (7.5 min); and glycine (to inhibit proteinase K) in PBS (3×5 min). Proteinase K was digested for 30 min at 37° C. before use. Sections were then incubated at 37° C. in 50% formamide, 750 mM NaCl, 25 mM EDTA, 0.2% SDS, 0.02% BSA, 0.002% Ficoll, 0.02% polyvinylpyrrolidone, 250 μg/ml yeast tRNA, 250 μg/ml poly A, and 25 mM PPES (pH 6.8).

For the hybridization, 100 mM DTT, 10% dextran sulfate, and sense or antisense $^{35}S$-RNA were added to the prehybridization solution. An aliquot (50 μl) of the hybridization solution containing about 3 ng ($10^6$ cpm) of probe (sense or antisense) was added onto the slides. Each slide was coverslipped and incubated for 16 hrs at 50° C., following which the siliconized coverslips were removed by brief washing in 4×SSC (1×SSC-150 mM NaCl, 60 mM Na citrate, pH 7.0).

Sections were then treated with ribonuclease A (50 μg/ml in 0.5M NaCl, 10 mM Na thiosulfate, 1 mM EDTA, 10 mM Tris HCL, pH 8.0) for 20 min at 37° C. and rinsed for 2 hrs at room temperature in 2×SSC, 10 mM Na thiosulfate, for 30 min at 55° C. Sections were dehydrated in ethanol, delipidated in xylene, coated with Kodak NTB2 emulsion and exposed for 10 days at 4° C. The emulsion was developed with Kodak D19, and the tissue counterstained with cresyl violet.

Autoradiographic grains were detected using reflected polarized light and grain numbers, densities, nd cell areas were determined with an Analytic Imaging Concepts image analyzer system. Due to the low background level, the criteria for defining a cell "labeled" was based on the presence of more than 5 clustered grains. The GAD labeled cells were found scattered throughout the brain, enabling the measurement of the number of grains over individual cells. The boundary of the cell and the area covered by a grain allowed the calculation of the number of grains per cell. This analysis was done at a high magnification (800×), using both reflected polarized light and transmitted light to simultaneously visualize the stained cell and the superimposed grains. Numbers are means±S.E.M. of "n" cells.

TABLE 2

| CELL TYPE | GRAINS/CELL | | |
|---|---|---|---|
| | $GAD_{67}$mRNA | $GAD_{65}$mRNA | $GAD_{67}$:$GAD_{65}$ |
| Purkinje | 172 ± 34 (87)[a] | 43 ± 2 (70) | 4.0 |
| Golgi II | 96 ± 8 (80) | 64 ± 9 (65) | 1.5 |
| Basket | 61 ± 12 (102) | 16 ± 1 (57) | 3.8 |
| Stellate | 55 ± 15 (65) | 18 ± 3 (37) | 3.1 |

[a] ±S.E.M.(n)

In all neuronal types $GAD_{67}$ mRNA levels are greater. The observations with in-situ hybridization are consistent with previous findings (Nitsch, *J. Neurochem.*, 34:822, 1980; Denner, et al., *J. Neurochem.*, 44:957, 1985; Itoh, et al., *Neurochem. Res.* 6:1283, 1981) that the ratio of PLP dependent to independent GAD activities in the cerebellum is one of the lowest in brain regions tested. In addition, as shown in Table 2, the order of amounts for $GAD_{67}$ mRNA is Purkinje>Golgi II>Basket>Stellate cells; in contrast, for $GAD_{65}$ mRNA, this order is Golgi II>Purkinje>Basket>Stellate cells.

The expression of $GAD_{65}$ and $GAD_{67}$ mRNAs thus differs among classes of neurons. The contribution of each to total GAD activity in turn affects how GABA production is regulated. For example, the substantia nigra contains one of the highest ratios of PLP dependent to PLP-independent GAD activities (Nitsch, *J. Neurochem.*, 34:822, 1980). Increasing GABA concentration in the substantia nigra by local injection of inhibitors of GABA catabolism is especially effective in reducing seizure susceptibility (Gale, *Fed. Proc.*, 44:2414, 1985). Experimental animals undergoing seizures induced by PLP-antagonists may therefore be unable to inhibit seizure propagation because of inhibition of $GAD_{65}$ particularly in nerve terminals within the substantia nigra.

F. Subcellular Location of $GAD_{65}$ and $GAD_{67}$

The distribution of $GAD_{65}$ and $GAD_{67}$ was evaluated in the $S_2$ and synaptosome subcellular fractions. $S_2$ is a high speed supernatant consisting of the cytosol of all cells in the brain, while the synaptosomal fraction consists primarily of nerve endings (Gray, et al., *J. Anat., Lond*, 96:79, 1962). For these studies, whole rat brain fractionation was performed as described by Booth and Clark (Booth, et al., *Biochem. J.*, 176:365, 1978). Protein concentrations were determined by Schaffner and Weissman (Schaffner, et al., *Anal. Biochem.* 56:502, 1973). Samples were prepared as described (Kaiser, et al., *DNA Cloning, Vol. I, A Practical Approach*, D. M. Glover ed. (IRL Press, Oxford, 1985, pp. 38-40), and immunoblotting was done as described above using GAD-6 monoclonal antibody and K-2 antiserum. Equal amounts of protein (16 μg) were added to each lane. Autoradiography showed a linear response of increasing amount of $^{125}$I-protein A bound to antibody with protein concentrations of 1, 3, 10, 30, 100 μgs with both K-2 antiserum and GAD-6 monoclonal antibody (data not shown).

The results showed that $GAD_{67}$ was present in equal amounts in both fractions. Since the $S_2$ fraction contains the cytosolic proteins of glial (as well as other non-neuronal) and neuronal cells, the concentration of $GAD_{67}$ must be greater in neuronal cell bodies than in nerve endings. In contrast, the concentration of $GAD_{65}$ was greater in synaptosomes than in $S_2$. These subcellular fractionation experiments suggest that, in contrast to $GAD_{65}$, a much greater fraction of $GAD_{67}$ is present in cell bodies of neurons than in nerve terminals. Thus, subcellular fractionation, like immuhohistochemistry, shows that $GAD_{65}$ and $GAD_{67}$ have different subcellular distributions.

In vivo experiments utilizing inhibitors of GABA synthesis and degradation have suggested that the GABA pool in neuronal cell bodies is different from that in the nerve terminals (Iadarola, et al., *Mol. Cell. Biochem.*, 39:305, 1981). GABA produced by $GAD_{67}$ may be involved more in cellular metabolism (for example, in the GABA shunt) and in dendrodendritic synapses. The dendrites of granule cells in the olfactory bulb, which form dendrodendritic synapses with mitral dendrites (Shepard, *Physiol. Rev.*, 52:864, 1972) and probably release GABA (McLennan, *Brain Res.*, 29:177-184, 1971), label intensely with K-2 antiserum. While not shown here, it has also been found greater $GAD_{67}$ than $GAD_{65}$ mRNA levels (2-3 fold) in the olfactory bulb. This distribution is consistent with the reported finding that most GAD activity in the olfactory bulb is present in $S_2$ and $P_1$ (crude nuclear pellet) and not in synaptosomes (Quinn, et al., *J. Neurochem.*, 35:583, 1980).

The differing subcellular distributions of $GAD_{65}$ and $GAD_{67}$ could result from cytoskeletal anchoring or from some unknown protein targeting mechanism. Some cytoskeletal proteins have distributions that resemble $GAD_{65}$ and $GAD_{67}$. For example, in cultured sympathetic neurons Peng, et al. (*J. Cell. Biol.*, 102:252, 1986), demonstrate that 84% of tau is in axons while 100% of MAP-2 is in cell bodies and dendrites. In addition, 43 kd protein, a cytoskeletal protein, is thought to anchor the acetylcholine receptor to the underlying membrane cytoskeleton (Flucher, et al., *Neuron*, 3:163, 1989).

EXAMPLE 3

Detection of Gad Autoantibodies in Clinical Specimens

A. Materials and Methods

1. Patient Specimens. Sera from four groups of individuals were selected from a previous study by Atkinson and co-workers (Atkinson, et al., *Lancet*, 335:1357-1360, 1990). These groups consisted of: Group (1), 1 new onset IDD patients diagnosed according to the established National Diabetes Data Group (NDDG) criteria (Gleichman, et al., *Diabetes*, 36:578-584, 1987) that had been referred to the University of Florida, Diabetes Clinics; Group (2), 5 randomly selected islet cell cytoplasmic antibody (ICA) negative non-diabetic controls without any known family history of autoimmune disease; Group (3), 13 individuals whose sera had been collected 3 to 66 months prior to their documented clinical onsets of IDD; Group (4), non-diabetic controls and relatives, and those who were studied prior to their onsets of IDD; and Group (5), 3 patients at risk for IDDM, but where onset has not yet occurred. This latter group had been ascertained through ongoing prospective ICA screening studies of more than 5000 first degree relative of IDD probands, and 8200 individuals from the general population (of which 4813 were school children).

2. Islet Cell Autoantibodies. ICA were assayed by indirect immunofluorescence on blood group O cryocut pancreatic (Atkinson, et al., *Lancet*, 335:1357-1360, 1990). All results were interpreted on coded samples, with control negative and positive sera in each batch. The degrees of ICA positivity were analyzed with the guidelines established by the Immunology Diabetes Workshop (IDW) for the standardization of ICA (Gleichman, et al., *Diabetes*, 36:578-584, 1987). All positive sera were titered by end point dilution, and the Juvenile Diabetes Foundation (JDF) units were determined by reference to a standard serum previously calibrated to the international JDF standard of 80 units. In the studies reported here, a positive ICA result was defined by replicate titers of 10 JDF units or greater.

3. HLA DR Typing. HLA DR typing was performed as adapted from the method described by Van Rood and Van Leuwen (*Nature*, 262:795-797, 1976), using DR trays (One Lamda Laboratories, Los Angeles, Calif.).

4. Human Islet Cells. Human pancreatic islets were isolated from cadaveric pancreases and maintained in vitro as previously described (Ricordi, et al., *Diabetes*, 37:413-420, 1988). The islet cells were metabolically labeled with $^{35}S$ methionine (Amersham, Arlington Heights, Ill.) in vitro (95% air/5% $CO_2$).

5. Islet Cell Extractions and Immunoprecipitations. Islet cells were extracted as previously described by Atkinson, et al. (*Lancet*, 335:1357-1360, 1990) with the following modifications. For immunoprecipitation studies, the islet cell lysates were precleared twice by incubation (2 h, 4° C.) with either control, IDD serum (100 µl), or GAD-6 (Chang, et al., *J. Neuro*, 8:2123-2130, 1988) (1 µl in 99 µl of Tris buffer (Atkinson, et al., *Lancet*, 335:1357-1360, 1990) for every 1000 islets. Immune complexes were then absorbed (1 h 4° C.) with an excess of protein A Sepharose CL-4B (Pharmacia, N.J.). Aliquot volumes representing 1000 islet cells containing unbound (precleared) lysate were then incubated (12 h, 4° C.) with either IDD or control sera (25 µl), or GAD-6 (Chang, et al., *J. Neuro*, 8:2123-2130, 1988) (1 µl in 25 µl Tris buffer). Following another incubation with protein A Sepharose CL-4B (1 h, 4° C.), the complexes were then washed 5 times with 50 mM Tris HCL (pH 7.4) with 0.1% SDS, 1.0% Triton X-114, and 2 mM EDTA, and then washed again one time in double distilled water. The protein A Sepharose CL-4B was then boiled in Laemmli sample buffer (Laemmli, *Nature*, 227:680-685, 1970), and the samples were subjected to SDS-PAGE and fluororadiography (Kodak, X-omat AR5) using Enhance (New England Nuclear). Alternatively, the autoradiographs were analyzed by a BETAGEN (Boston, Mass.) analyzer. Both 64KA positive and negative sera were used in each assay, to serve as interassay controls. All fluororadiographs were analyzed and rated as positive or negative after comparison with the known interassay controls. Positive serum samples were designated as 1 when a sample resulted in immunoprecipitation of a low intensity 64,000 $M_x$ band, 2 if a moderate intensity band was observed and 3 if the intensity of the immunoprecipitated protein was high. A similar rating procedure was employed for the intensity of bands corresponding to immunoprecipitated $^{35}S$-$GAD_{65}$ and $^{35}S$-$GAD_{67}$.

6. Immunoprecipitations. Immunoprecipitation of bacterial lysates containing $^{35}S$-$GAD_{65}$ or $^{35}S$-$GAD_{67}$, and GAD from human brain homogenate, was completed as described above in immunoprecipitation studies of human islet cell extractions.

7. GAD Assays. Human brain homogenates were incubated with patient sera as described above in human islet cells. After absorption and washes, the protein A agarose slurry was aliquoted into three equal volumes and GAD activity was measured as described (Krieger, et al., *Neurochem.* 33:299, 1984). Briefly, Protein A agarose beads were incubated with (1-$^{14}C$)-glutamate (Amersham) in a designated incubation mixture (Krieger, et al., *Neurochem.*

33:299, 1984) and production of $^{14}CO_2$ was quantitated by a liquid scintillation counter.

8. Production of $^{35}S$-$GAD_{65}$ and $^{35}S$-$GAD_{67}$. Rat $GAD_{65}$ and $GAD_{67}$ cDNAs were subcloned into a bacterial expression system as previously described. Labeling of $^{35}S$-GADs was completed by pulsing IPTG induced bacterium (growing in Minimal Media) for 15 minutes with TRAN $^{35}S$-label (ICN). Cultures were then spun down and resuspended and sonicated in 1 ml of homogenizing buffer (1 mM phenylmethylsulfonyl fluoride (PMSF), 1 mM 2-aminoethylisothiouronium Bromide (AET) and 60 mM potassium phosphate, pH 7.1). After sonication, cell debris was removed by centrifugation and protein concentration was measured (Bradford, *Anal. Biochem.*, 72:248, 1986) in the supernatant (supernatant was stored in aliquots at −70° C.).

B. Immunoreactivity of IDDM Specimens

Sera from patients with IDDM were tested for the ability to precipitate GAD from human brain homogenates.

TABLE 3

SERA FROM IDDM PATIENTS IMMUNOPRECIPITATE GAD ACTIVITY

| Patient | IDDM | Pre-IDDM Period[1] | 64K[2] | JDF[3] | GAD Activity[4] cpm's |
|---|---|---|---|---|---|
| DA | *[5] | >24 | 3 | 164 | 13,762 |
| DC | * | >1 | 3 | 20 | 1,719 |
| RS | + | 5 | 3 | 40 | 588 |
| NL | + | 0 | 2 | 80 | 440 |
| DM | * | >1 | 2 | 10 | 184 |
| C | − | na | 0 | 0 | 280 |
| C | − | na | 0 | 0 | 285 |
| C | − | na | 0 | 0 | 325 |
| C | − | na | 0 | 0 | 275 |
| C | − | na | 0 | 0 | 270 |

[1]Expressed as months
[2]64K titers as described in Experimental Methods
[3]The islet cell antibody test as expressed in Juvenile Diabetes Foundation (JDF) units
[4]Not adjusted for background
[5]At risk for diabetes (also, failed glucose test)
na—Not applicable As shown in Table 3, the sera of four (out of five) at risk for IDDM or IDDM patients bound significantly greater amounts of enzymatically active GAD of human brain extracts than sera from control patients. In addition, sera from one of the patients was drawn in a pre-IDDM period, thus autoantibodies to GAD are present prior to the onset of IDDM symptoms (see C below).

Further experiments (results not presented) showed that the sera of two at risk IDDM patients (DA, DC) immunoprecipitated recombinantly produced $^{35}S$-$GAD_{65}$ whereas recombinantly produced $^{35}S$-$GAD_{67}$ was only recognized by sera of patient DA (and to a lesser degree than $^{35}S$-$GAD_{65}$). Subsequent studies have found larger titers of $GAD_{67}$ autoantibodies than $GAD_{65}$ are present in sera of IDDM patients with neuropathic complications (not shown here).

Additional studies using patient DA sera showed the presence of antibodies which recognize specific polypeptides produced in human pancreatic islet cells. Electrophoretic analysis of the bound polypeptides demonstrated the presence of autoantibodies to a 64 kD component, as previously shown by others in human IDDM (Baekkeskov, et al., *Nature*, 298:167-169, 1982) and in animal models (Baekkeskov, et al., *Science*, 224:1348-1350, 1984; Atkinson, et al., *Diabetes*, 37:1587-1590, 1988). Prior absorption of these sera with GAD-6 monoclonal, which recognized $GAD_{65}$ but not $GAD_{67}$, or with bacterially produced $GAD_{65}$, abolished the ability of the sera to recognize the 64 kD pancreatic polypeptide. The epitopes recognized by autoantibodies to the 64 kD autoantigen are thus present in $GAD_{65}$, indicating that the autoantigen is indeed $GAD_{65}$. In order to investigate the predictive value of $GAD_{65}$, sera drawn from patients prior to onset of clinical manifestation of IDDM were tested for autoantibodies to $GAD_{65}$.

TABLE 4

IDDM PATIENTS ANALYZED FOR AUTOANTIBODIES PRIOR TO THE ONSET OF DISEASE

| Patient | Sex | HLA | Age Onset[1] | Pre-IDD Period[2] | JDF | 64KA[3] | $GAD^3_{65}$ | $GAD^3_{67}$ |
|---|---|---|---|---|---|---|---|---|
| TA | M | 3, 2 | 17 | 11 | 20 | 2 | 0 | 1 |
| CA | F | 4, 5 | 38 | 4 | 0 | 1 | 1 | 0 |
| RA | M | 2, 1 | 5 | 34 | 0 | 2 | 1 | 0 |
| TB | M | 2, 4 | 11 | 66 | 40 | 1 | 1 | 0 |
| AB | M | N.D. | 23 | 6 | 160 | 3 | 3 | 2 |
| VC | F | 4, 6 | 15 | 3 | 40 | 1 | 0 | 1 |
| JD | M | 6, 1 | 34 | 25 | 10 | 3 | 1 | 1 |
| DR | F | 3, 4 | 14 | 42 | 320 | 2 | 1 | 0 |
| JG | M | 3, 3 | 12 | 8 | 40 | 1 | 0 | 0 |
| BR | M | 3, 3 | 5 | 9 | 0 | 0 | 1 | 1 |
| KR | F | 4, X | 34 | 14 | 10 | 3 | 2 | 0 |
| JT | F | 4, 6 | 7 | 10 | N.D. | 1 | 1 | 1 |

[1]Age of IDDM onset expressed as months
[2]The time interval between sera drawn and IDDM onset expressed as months
[3]1 = lowest; 2 = medium; and 3 = highest band intensities
N.D.—not determined As shown in Table 4, 9 out of 12 specimens (75%) were immunoreactive with $^{35}S$-$GAD_{65}$. In addition, two patients (JA and VC) were immunoreactive to $GAD_{67}$, but not $GAD_{65}$ under these conditions. Therefore, in combination, autoantibodies to $GAD_{65}$ and $GAD_{67}$ were present in 11 out of 12 (91%) of these patients sera. This finding suggests that although autoantibodies to $GAD_{65}$ are more common than autoantibodies to $GAD_{67}$, the use of both recombinant GADs ($GAD_{65}$ and $GAD_{67}$) in an assay would allow for greater predictability of IDDM. Previous tests of these sera (Atkinson, et al., *Langet,* 335:1357-1360, 1990) demonstrated that 11 out of 12, or 92%, immunoreacted with the $^{35}S$-64 kD molecule from human pancreatic islet cells. The serum which contained detectable autoantibodies to the 64 kD molecule and not $GAD_{65}$ was a serum which contained the lowest titer (or "1") for the 64 kD molecule. Thus, the false negative obtained was due to a lack of sensitivity in this assay. Furthermore, this assay predicted IDDM in one patient (BR) who was negative for 64K.

These results show that the 64 kD molecule identified in α-cells of human pancreas is identical in size and antigenicity to rat $GAD_{65}$. Furthermore, sera drawn from patients prior to IDDM onset contain autoantibodies to $GAD_{65}$. Consequently, the $GAD_{65}$ recombinant molecule is of great utility as a diagnostic tool for predicting IDDM. The ability of a physician to diagnose IDDM prior to actual symptoms will no doubt result in a greater extension of time before insulin therapy is needed. The sensitivity of such immunoassays will improve with the use of a recombinant $GAD_{65}$ of human origin which represents the GAD form present in β-cells of the pancreas.

The invention now being fully described, it will be apparent to one of ordinary skill in the art that many changes and modifications can be made without departing from the spirit or scope of the invention.

The invention claimed is:

1. An isolated nucleic acid sequence encoding a polypeptide having an amino acid sequence consisting of a sequence present in the glutamic acid decarboxylase65 ($GAD_{65}$) of FIG. 2 (SEQ ID NO:5) or FIG. 3 (SEQ ID NO:8) and possessing at least one epitope for an autoantibody to $GAD_{65}$, wherein said epitope is present in $GAD_{65}$ but not $GAD_{67}$.

2. The isolated nucleic acid sequence of claim 1, wherein said sequence possesses a single epitope for an autoantibody to $GAD_{65}$.

3. The isolated nucleic acid sequence of claim 1, wherein said sequence is a cDNA sequence.

4. An isolated host cell transformed or transfected with the nucleic acid sequence of claim 1.

5. The nucleic acid of claim 1, wherein said nucleic acid encodes an epitope which binds serum from an IDDM patient.

6. The nucleic acid of claim 1, wherein said nucleic acid encodes the amino terminal 100 amino acids of $GAD_{65}$.

* * * * *

SEQUENCE LISTING

<160> NUMBER OF SEQ ID NOS: 8

<210> SEQ ID NO 1
<211> LENGTH: 60
<212> TYPE: PRT
<213> ORGANISM: Felis

<400> SEQUENCE: 1

Tyr Glu Ile Ala Pro Val Phe Val Leu Met Glu Gln Ile Thr Leu Lys
 1               5                  10                  15

Lys Met Arg Glu Ile Val Gly Trp Ser Ser Lys Asp Gly Asp Gly Ile
            20                  25                  30

Phe Ser Pro Gly Gly Ala Ile Ser Asn Met Tyr Ser Ile Met Ala Ala
        35                  40                  45

Arg Tyr Lys Phe Phe Pro Glu Val Lys Thr Lys Gly
    50                  55                  60

<210> SEQ ID NO 2
<211> LENGTH: 53
<212> TYPE: PRT
<213> ORGANISM: Mus musculus

<400> SEQUENCE: 2

Tyr Glu Ile Ala Pro Val Phe Val Leu Leu Glu Tyr Val Arg Glu Ile
 1               5                  10                  15

Ile Gly Trp Pro Gly Gly Ser Asp Gly Ile Phe Ser Pro Gly Gly Ala
            20                  25                  30

Ile Ser Asn Tyr Ala Met Leu Ile Ala Arg Tyr Lys Met Phe Pro Glu
        35                  40                  45

Val Lys Glu Lys Gly
    50

<210> SEQ ID NO 3
<211> LENGTH: 1966
<212> TYPE: DNA
<213> ORGANISM: Mus musculus

<400> SEQUENCE: 3
gggcgtgcgg ggtcgagccg aagcagcttg cccgcagcca ctcggaggcg accagcgcca      60
gactagcaga acccatggca tctccgggct ctggcttttg gtccttcgga tctgaagatg     120
gctctgggga tcctgagaac ccgggaacag cgagagcctg tgccaggtg gcccaaaagt      180 tcacgggcgg catcggaaac aagctatgcg ctctgctcta cggagactct gagaagccag     240
cagagagcgg cgggagcgtg acctcgcggg ccgccactcg gaaggtcgcc tgcacctgtg     300
accaaaaacc ctgcagctgc cccaaaggag atgtcaatta tgcacttctc cacgcaacag     360
acctgctgcc agcctgtgaa ggagaaaggc ccactctcgc atttctgcaa gatgtaatga     420 acatttttgct tcagtacgtg gtgaaaagtt ttgatagatc aactaaagtg attgatttcc     480
attaccccaa tgagcttctt caagagtata attgggaatt ggcagaccaa ccgcaaaatc     540
tggaggaaat tttgacgcac tgccaaacaa ctctaaaata tgcgattaaa acagggcatc     600
cccgatattt taatcagctg tctaccggat ggatatggt tggattagca gcagattggt      660
tgacatcaac agcaaacacg aacatgttta cctatgagat cgcccctgta tttgtactac     720
tggaatatgt gacactaaag aaaatgaggg aaatcattgg ctggccagga ggctctggcg     780
atggaatctt ttctcctggt ggtgccatct ccaacatgta cgccatgctc attgcccgct     840

-continued

```
ataagatgtt tccagaagtc aaggaaaagg ggatggcggc ggtgcccagg ctcatcgcat    900
tcacgtcaga gcatagtcac ttttctctca agaagggagc tgcagccttg gggatcggaa    960
cagacagcgt gattctgatt aaatgtgatg agagagggaa aatgatccca tctgaccttg   1020
aaagaagaat ccttgaagtc aaacagaaag gatttgttcc tttcctggtg agtgccacag   1080
ctggaaccac tgtgtacggg gcttttgatc ctctcttggc tgtagctgac atctgcaaaa   1140
aatataagat ctggatgcat gtggatgctg cttggggtgg agggttactg atgtctcgga   1200
aacacaagtg gaagctgaac ggtgtggaga gggccaactc tgtgacatgg aatccccaca   1260
agatgatggg tgtccccttg caatgttcgg ctctcctggt cagagaggag ggactgatgc   1320
agagctgcaa ccagatgcat gcttcctacc tctttcagca agataagcac tatgacctgt   1380
cctatgacac gggagacaag gccttgcagt gtggacgcca cgtcgatgtc tttaaattat   1440
ggctcatgtg gagagcaaag gggactactg gatttgaagc tcacattgat aagtgtttgg   1500
agctggcaga gtatttatac aatatcatta aaaaccgaga aggatatgaa atggtgttcg   1560 atggggaagcc tcagcacaca aatgtctgct tctggttttgt acctcctagt ttgcgagttc   1620
tggaagacaa tgaagagaga atgagccgcc tctcaaaggt ggcgccagtg attaaagcca   1680
gaatgatgga gtatgggacc acaatggtca gctaccaacc cttaggagat aaggtcaact   1740
tcttccgcat ggtcatctca aaccctgcag caactcacca agacattgac ttcctcattg   1800
aagaaatcga acgcctggga caagatttgt aatcactttg ctcaccaaac tttcagttct   1860
ctaggtagac agctaagttg tcacaaactg tgtaaatgta tttgtagttt gttccagagt   1920
aattctattt ctatatcgtg gtgtcacagt agagtccagt ttaaaa               1966
```

```
<210> SEQ ID NO 4
<211> LENGTH: 1758
<212> TYPE: DNA
<213> ORGANISM: Mus musculus
<220> FEATURE:
<221> NAME/KEY: CDS
<222> LOCATION: (1)...(1758)

<400> SEQUENCE: 4 atg gca tct ccg ggc tct ggc ttt tgg tcc ttc gga tct gaa gat ggc      48
Met Ala Ser Pro Gly Ser Gly Phe Trp Ser Phe Gly Ser Glu Asp Gly
1               5                   10                  15 tct ggg gat cct gag aac ccg gga aca gcg aga gcc tgg tgc cag gtg      96
Ser Gly Asp Pro Glu Asn Pro Gly Thr Ala Arg Ala Trp Cys Gln Val
            20                  25                  30 gcc caa aag ttc acg ggc ggc atc gga aac aag cta tgc gct ctg ctc     144
Ala Gln Lys Phe Thr Gly Gly Ile Gly Asn Lys Leu Cys Ala Leu Leu
        35                  40                  45 tac gga gac tct gag aag cca gca gag agc ggc ggg agc gtg acc tcg     192
Tyr Gly Asp Ser Glu Lys Pro Ala Glu Ser Gly Gly Ser Val Thr Ser
    50                  55                  60 cgg gcc gcc act cgg aag gtc gcc tgc acc tgt gac caa aaa ccc tgc     240
Arg Ala Ala Thr Arg Lys Val Ala Cys Thr Cys Asp Gln Lys Pro Cys
65                  70                  75                  80 agc tgc ccc aaa gga gat gtc aat tat gca ctt ctc cac gca aca gac     288
Ser Cys Pro Lys Gly Asp Val Asn Tyr Ala Leu Leu His Ala Thr Asp
                85                  90                  95 ctg ctg cca gcc tgt gaa gga gaa agg ccc act ctc gca ttt ctg caa     336
Leu Leu Pro Ala Cys Glu Gly Glu Arg Pro Thr Leu Ala Phe Leu Gln
            100                 105                 110 gat gta atg aac att ttg ctt cag tac gtg gtg aaa agt ttt gat aga     384
```

|   |   |   |   |   |   |   |   |   |   |   |   |   |   |   |   |
|---|---|---|---|---|---|---|---|---|---|---|---|---|---|---|---|
| Asp | Val | Met | Asn | Ile | Leu | Leu | Gln | Tyr | Val | Val | Lys | Ser | Phe | Asp | Arg |
|  |  | 115 |  |  |  | 120 |  |  |  | 125 |  |  |  |  |  |

```
tca act aaa gtg att gat ttc cat tac ccc aat gag ctt ctt caa gag           432
Ser Thr Lys Val Ile Asp Phe His Tyr Pro Asn Glu Leu Leu Gln Glu
    130             135             140 tat aat tgg gaa ttg gca gac caa ccg caa aat ctg gag gaa att ttg           480
Tyr Asn Trp Glu Leu Ala Asp Gln Pro Gln Asn Leu Glu Glu Ile Leu
145             150             155             160 acg cac tgc caa aca act cta aaa tat gcg att aaa aca ggg cat ccc           528
Thr His Cys Gln Thr Thr Leu Lys Tyr Ala Ile Lys Thr Gly His Pro
                165             170             175 cga tat ttt aat cag ctg tct acc gga ttg gat atg gtt gga tta gca           576
Arg Tyr Phe Asn Gln Leu Ser Thr Gly Leu Asp Met Val Gly Leu Ala
            180             185             190 gca gat tgg ttg aca tca aca gca aac acg aac atg ttt acc tat gag           624
Ala Asp Trp Leu Thr Ser Thr Ala Asn Thr Asn Met Phe Thr Tyr Glu
        195             200             205 atc gcc cct gta ttt gta cta ctg gaa tat gtg aca cta aag aaa atg           672
Ile Ala Pro Val Phe Val Leu Leu Glu Tyr Val Thr Leu Lys Lys Met
    210             215             220 agg gaa atc att ggc tgg cca gga ggc tct ggc gat gga atc ttt tct           720
Arg Glu Ile Ile Gly Trp Pro Gly Gly Ser Gly Asp Gly Ile Phe Ser
225             230             235             240 cct ggt ggt gcc atc tcc aac atg tac gcc atg ctc att gcc cgc tat           768
Pro Gly Gly Ala Ile Ser Asn Met Tyr Ala Met Leu Ile Ala Arg Tyr
                245             250             255 aag atg ttt cca gaa gtc aag gaa aag ggg atg gcg gcg gtg ccc agg           816
Lys Met Phe Pro Glu Val Lys Glu Lys Gly Met Ala Ala Val Pro Arg
            260             265             270 ctc atc gca ttc acg tca gag cat agt cac ttt tct ctc aag aag gga           864
Leu Ile Ala Phe Thr Ser Glu His Ser His Phe Ser Leu Lys Lys Gly
        275             280             285 gct gca gcc ttg ggg atc gga aca gac agc gtg att ctg att aaa tgt           912
Ala Ala Ala Leu Gly Ile Gly Thr Asp Ser Val Ile Leu Ile Lys Cys
    290             295             300 gat gag aga ggg aaa atg atc cca tct gac ctt gaa aga aga atc ctt           960
Asp Glu Arg Gly Lys Met Ile Pro Ser Asp Leu Glu Arg Arg Ile Leu
305             310             315             320 gaa gtc aaa cag aaa gga ttt gtt cct ttc ctg gtg agt gcc aca gct          1008
Glu Val Lys Gln Lys Gly Phe Val Pro Phe Leu Val Ser Ala Thr Ala
                325             330             335 gga acc act gtg tac ggg gct ttt gat cct ctc ttg gct gta gct gac          1056
Gly Thr Thr Val Tyr Gly Ala Phe Asp Pro Leu Leu Ala Val Ala Asp
            340             345             350 atc tgc aaa aaa tat aag atc tgg atg cat gtg gat gct gct tgg ggt          1104
Ile Cys Lys Lys Tyr Lys Ile Trp Met His Val Asp Ala Ala Trp Gly
        355             360             365 gga ggg tta ctg atg tct cgg aaa cac aag tgg aag ctg aac ggt gtg          1152
Gly Gly Leu Leu Met Ser Arg Lys His Lys Trp Lys Leu Asn Gly Val
    370             375             380 gag agg gcc aac tct gtg aca tgg aat ccc cac aag atg atg ggt gtc          1200
Glu Arg Ala Asn Ser Val Thr Trp Asn Pro His Lys Met Met Gly Val
385             390             395             400 ccc ttg caa tgt tcg gct ctc ctg gtc aga gag gag gga ctg atg cag          1248
Pro Leu Gln Cys Ser Ala Leu Leu Val Arg Glu Glu Gly Leu Met Gln
                405             410             415 agc tgc aac cag atg cat gct tcc tac ctc ttt cag caa gat aag cac          1296
Ser Cys Asn Gln Met His Ala Ser Tyr Leu Phe Gln Gln Asp Lys His
            420             425             430
```

```
tat gac ctg tcc tat gac acg gga gac aag gcc ttg cag tgt gga cgc      1344
Tyr Asp Leu Ser Tyr Asp Thr Gly Asp Lys Ala Leu Gln Cys Gly Arg
            435                 440                 445 cac gtc gat gtc ttt aaa tta tgg ctc atg tgg aga gca aag ggg act      1392
His Val Asp Val Phe Lys Leu Trp Leu Met Trp Arg Ala Lys Gly Thr
    450                 455                 460 act gga ttt gaa gct cac att gat aag tgt ttg gag ctg gca gag tat      1440
Thr Gly Phe Glu Ala His Ile Asp Lys Cys Leu Glu Leu Ala Glu Tyr
465                 470                 475                 480 tta tac aat atc att aaa aac cga gaa gga tat gaa atg gtg ttc gat      1488
Leu Tyr Asn Ile Ile Lys Asn Arg Glu Gly Tyr Glu Met Val Phe Asp
                485                 490                 495 ggg aag cct cag cac aca aat gtc tgc ttc tgg ttt gta cct cct agt      1536
Gly Lys Pro Gln His Thr Asn Val Cys Phe Trp Phe Val Pro Pro Ser
            500                 505                 510 ttg cga gtt ctg gaa gac aat gaa gag aga atg agc cgc ctc tca aag      1584
Leu Arg Val Leu Glu Asp Asn Glu Glu Arg Met Ser Arg Leu Ser Lys
        515                 520                 525 gtg gcg cca gtg att aaa gcc aga atg atg gag tat ggg acc aca atg      1632
Val Ala Pro Val Ile Lys Ala Arg Met Met Glu Tyr Gly Thr Thr Met
530                 535                 540 gtc agc tac caa ccc tta gga gat aag gtc aac ttc ttc cgc atg gtc      1680
Val Ser Tyr Gln Pro Leu Gly Asp Lys Val Asn Phe Phe Arg Met Val
545                 550                 555                 560 atc tca aac cct gca gca act cac caa gac att gac ttc ctc att gaa      1728
Ile Ser Asn Pro Ala Ala Thr His Gln Asp Ile Asp Phe Leu Ile Glu
                565                 570                 575 gaa atc gaa cgc ctg gga caa gat ttg taa                              1758
Glu Ile Glu Arg Leu Gly Gln Asp Leu *
            580                 585

<210> SEQ ID NO 5
<211> LENGTH: 585
<212> TYPE: PRT
<213> ORGANISM: Mus musculus

<400> SEQUENCE: 5

Met Ala Ser Pro Gly Ser Gly Phe Trp Ser Phe Gly Ser Glu Asp Gly
 1               5                  10                  15

Ser Gly Asp Pro Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ser Glu Lys Pro Ala Glu Ser Gly Gly Ser Val Thr Ser
    50                  55                  60

Arg Ala Ala Thr Arg Lys Val Ala Cys Thr Cys Asp Gln Lys Pro Cys
65                  70                  75                  80

Ser Cys Pro Lys Gly Asp Val Asn Tyr Ala Leu Leu His Ala Thr Asp
                85                  90                  95

Leu Leu Pro Ala Cys Glu Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
    130                 135                 140

Tyr Asn Trp Glu Leu Ala Asp Gln Pro Gln Asn Leu Glu Glu Ile Leu
145                 150                 155                 160

Thr His Cys Gln Thr Thr Leu Lys Tyr Ala Ile Lys Thr Gly His Pro
```

```
                165                 170                 175
Arg Tyr Phe Asn Gln Leu Ser Thr Gly Leu Asp Met Val Gly Leu Ala
            180                 185                 190
Ala Asp Trp Leu Thr Ser Thr Ala Asn Thr Asn Met Phe Thr Tyr Glu
            195                 200                 205
Ile Ala Pro Val Phe Val Leu Glu Tyr Val Thr Leu Lys Lys Met
    210                 215                 220
Arg Glu Ile Ile Gly Trp Pro Gly Gly Ser Gly Asp Gly Ile Phe Ser
225                 230                 235                 240
Pro Gly Gly Ala Ile Ser Asn Met Tyr Ala Met Leu Ile Ala Arg Tyr
                245                 250                 255
Lys Met Phe Pro Glu Val Lys Glu Lys Gly Met Ala Ala Val Pro Arg
            260                 265                 270
Leu Ile Ala Phe Thr Ser Glu His Ser His Phe Ser Leu Lys Lys Gly
            275                 280                 285
Ala Ala Ala Leu Gly Ile Gly Thr Asp Ser Val Ile Leu Ile Lys Cys
            290                 295                 300
Asp Glu Arg Gly Lys Met Ile Pro Ser Asp Leu Glu Arg Arg Ile Leu
305                 310                 315                 320
Glu Val Lys Gln Lys Gly Phe Val Pro Phe Leu Val Ser Ala Thr Ala
                325                 330                 335
Gly Thr Thr Val Tyr Gly Ala Phe Asp Pro Leu Leu Ala Val Ala Asp
            340                 345                 350
Ile Cys Lys Lys Tyr Lys Ile Trp Met His Val Asp Ala Ala Trp Gly
            355                 360                 365
Gly Gly Leu Leu Met Ser Arg Lys His Lys Trp Lys Leu Asn Gly Val
            370                 375                 380
Glu Arg Ala Asn Ser Val Thr Trp Asn Pro His Lys Met Met Gly Val
385                 390                 395                 400
Pro Leu Gln Cys Ser Ala Leu Leu Val Arg Glu Glu Gly Leu Met Gln
                405                 410                 415
Ser Cys Asn Gln Met His Ala Ser Tyr Leu Phe Gln Gln Asp Lys His
            420                 425                 430
Tyr Asp Leu Ser Tyr Asp Thr Gly Asp Lys Ala Leu Gln Cys Gly Arg
            435                 440                 445
His Val Asp Val Phe Lys Leu Trp Leu Met Trp Arg Ala Lys Gly Thr
    450                 455                 460
Thr Gly Phe Glu Ala His Ile Asp Lys Cys Leu Glu Leu Ala Glu Tyr
465                 470                 475                 480
Leu Tyr Asn Ile Ile Lys Asn Arg Glu Gly Tyr Glu Met Val Phe Asp
                485                 490                 495
Gly Lys Pro Gln His Thr Asn Val Cys Phe Trp Phe Val Pro Pro Ser
            500                 505                 510
Leu Arg Val Leu Glu Asp Asn Glu Glu Arg Met Ser Arg Leu Ser Lys
            515                 520                 525
Val Ala Pro Val Ile Lys Ala Arg Met Met Glu Tyr Gly Thr Thr Met
            530                 535                 540
Val Ser Tyr Gln Pro Leu Gly Asp Lys Val Asn Phe Phe Arg Met Val
545                 550                 555                 560
Ile Ser Asn Pro Ala Ala Thr His Gln Asp Ile Asp Phe Leu Ile Glu
                565                 570                 575
Glu Ile Glu Arg Leu Gly Gln Asp Leu
            580                 585
```

<210> SEQ ID NO 6
<211> LENGTH: 2100
<212> TYPE: DNA
<213> ORGANISM: Homo sapiens

<400> SEQUENCE: 6

```
agctcgcccg cagctcgcac tcgcaggcga cctgctccag tctccaaagc cgatggcatc      60
tccgggctct ggcttttggt ctttcgggtc ggaagatggc tctggggatt ccgagaatcc     120
cggcacagcg cgagcctggt gccaagtggc tcagaagttc acgggcggca tcggaaacaa     180
actgtgcgcc ctgctctacg gagacgccga gaagccggcg gagagcggcg ggagccaacc     240
cccgcgggcc gccgcccgga aggccgcctg cgcctgcgac cagaagccct gcagctgctc     300
caaagtggat gtcaactacg cgtttctcca tgcaacagac ctgctgccgg cgtgtgatgg     360
agaaaggccc actttggcgt ttctgcaaga tgttatgaac attttacttc agtatgtggt     420
gaaaagtttc gatagatcaa ccaaagtgat tgatttccat tatcctaatg agcttctcca     480
agaatataat tgggaattgg cagaccaacc acaaaatttg gaggaaattt tgatgcattg     540
ccaaacaact ctaaaatatg caattaaaac agggcatcct agatacttca atcaactttc     600
tactggtttg gatatggttg gattagcagc agactggctg acatcaacag caaatactaa     660
catgttcacc tatgaaattg ctccagtatt tgtgcttttg gaatatgtca cactaaagaa     720
aatgagagaa atcattggct ggccaggggg ctctggcgat gggatatttt ctcccggtgg     780
cgccatatct aacatgtatg ccatgatgat cgcacgcttt aagatgttcc cagaagtcaa     840
ggagaaagga atggctgctc ttcccaggct cattgccttc acgtctgaac atagtcattt     900
ttctctcaag aagggagctg cagccttagg gattggaaca gacagcgtga ttctgattaa     960
atgtgatgag agagggaaaa tgattccatc tgatcctgaa agaaggattc ttgaagccaa    1020
acagaaaggg tttgttccctt tcctcgtgag tgccacagct ggaaccaccg tgtacggagc    1080
atttgacccc ctcttagctg tcgctgacat ttgcaaaaag tataagatct ggatgcatgt    1140
ggatgcagct tggggtgggg gattactgat gtcccgaaaa cacaagtgga aactgagtgg    1200
cgtggagagg gccaactctg tgacgtggaa tccacacaag atgatgggag tcccttttgca    1260
gtgctctgct ctcctggtta gagaagaggg attgatgcag aattgcaacc aaatgcatgc    1320
ctcctacctc tttcagcaag ataaacatta tgacctgtcc tatgacactg agacaaggc     1380
cttacagtgc ggacgccacg ttgatgtttt taaactatgg ctgatgtgga gggcaaaggg    1440
gactaccggg tttgaagcgc atgttgataa atgtttggag ttggcagagt atttatacaa    1500
catcataaaa aaccgagaag gatatgagat ggtgtttgat gggaagcctc agcacacaaa    1560
tgtctgcttc tggtacattc ctccaagctt gcgtactctg aagacaatg aagagagaat    1620
gagtcgcctc tcgaaggtgg ctccagtgat taaagccaga atgatggagt atggaaccac    1680
aatggtcagc taccaaccct tgggagacaa ggtcaatttc ttccgcatgg tcatctcaaa    1740
cccagcggca actcaccaag acattgactt cctgattgaa gaaatagaac gccttggaca    1800
agatttataa taaccttgct caccaagctg ttccacttct ctaggtagac aattaagttg    1860
tcacaaactg tgtgaatgta tttgtagttt gttccaaagt aaatctattt ctatattgtg    1920
gtgtcaaagt agagtttaaa aattaaacaa aaaagacatt gctccttta aaagtccttt     1980
cttaagtttta gaatacctct ctaagaattc gtgacaaaag gctatgttct aatcaataag    2040
gaaaagctta aaattgttat aaatacttcc cttactttta atatagtgtg caaagcaaac    2100
```

```
<210> SEQ ID NO 7
<211> LENGTH: 1758
<212> TYPE: DNA
<213> ORGANISM: Homo sapiens
<220> FEATURE:
<221> NAME/KEY: CDS
<222> LOCATION: (1)...(1758)

<400> SEQUENCE: 7 atg gca tct ccg ggc tct ggc ttt tgg tct ttc ggg tcg gaa gat ggc      48
Met Ala Ser Pro Gly Ser Gly Phe Trp Ser Phe Gly Ser Glu Asp Gly
  1               5                  10                  15 tct ggg gat tcc gag aat ccc ggc aca gcg cga gcc tgg tgc caa gtg      96
Ser Gly Asp Ser Glu Asn Pro Gly Thr Ala Arg Ala Trp Cys Gln Val
             20                  25                  30 gct cag aag ttc acg ggc ggc atc gga aac aaa ctg tgc gcc ctg ctc     144
Ala Gln Lys Phe Thr Gly Gly Ile Gly Asn Lys Leu Cys Ala Leu Leu
         35                  40                  45 tac gga gac gcc gag aag ccg gcg gag agc ggg agc caa ccc ccg         192
Tyr Gly Asp Ala Glu Lys Pro Ala Glu Ser Gly Ser Gln Pro Pro
     50                  55                  60 cgg gcc gcc gcc cgg aag gcc gcc tgc gcc tgc gac cag aag ccc tgc     240
Arg Ala Ala Ala Arg Lys Ala Ala Cys Ala Cys Asp Gln Lys Pro Cys
 65                  70                  75                  80 agc tgc tcc aaa gtg gat gtc aac tac gcg ttt ctc cat gca aca gac     288
Ser Cys Ser Lys Val Asp Val Asn Tyr Ala Phe Leu His Ala Thr Asp
                 85                  90                  95 ctg ctg ccg gcg tgt gat gga gaa agg ccc act ttg gcg ttt ctg caa     336
Leu Leu Pro Ala Cys Asp Gly Glu Arg Pro Thr Leu Ala Phe Leu Gln
            100                 105                 110 gat gtt atg aac att tta ctt cag tat gtg gtg aaa agt ttc gat aga     384
Asp Val Met Asn Ile Leu Leu Gln Tyr Val Val Lys Ser Phe Asp Arg
        115                 120                 125 tca acc aaa gtg att gat ttc cat tat cct aat gag ctt ctc caa gaa     432
Ser Thr Lys Val Ile Asp Phe His Tyr Pro Asn Glu Leu Leu Gln Glu
    130                 135                 140 tat aat tgg gaa ttg gca gac caa cca caa aat ttg gag gaa att ttg     480
Tyr Asn Trp Glu Leu Ala Asp Gln Pro Gln Asn Leu Glu Glu Ile Leu
145                 150                 155                 160 atg cat tgc caa aca act cta aaa tat gca att aaa aca ggg cat cct     528
Met His Cys Gln Thr Thr Leu Lys Tyr Ala Ile Lys Thr Gly His Pro
                165                 170                 175 aga tac ttc aat caa ctt tct act ggt ttg gat atg gtt gga tta gca     576
Arg Tyr Phe Asn Gln Leu Ser Thr Gly Leu Asp Met Val Gly Leu Ala
            180                 185                 190 gca gac tgg ctg aca tca aca gca aat act aac atg ttc acc tat gaa     624
Ala Asp Trp Leu Thr Ser Thr Ala Asn Thr Asn Met Phe Thr Tyr Glu
        195                 200                 205 att gct cca gta ttt gtg ctt ttg gaa tat gtc aca cta aag aaa atg     672
Ile Ala Pro Val Phe Val Leu Leu Glu Tyr Val Thr Leu Lys Lys Met
    210                 215                 220 aga gaa atc att ggc tgg cca ggg ggc tct ggc gat ggg ata ttt tct     720
Arg Glu Ile Ile Gly Trp Pro Gly Gly Ser Gly Asp Gly Ile Phe Ser
225                 230                 235                 240 ccc ggt ggc gcc ata tct aac atg tat gcc atg atg atc gca cgc ttt     768
Pro Gly Gly Ala Ile Ser Asn Met Tyr Ala Met Met Ile Ala Arg Phe
                245                 250                 255 aag atg ttc cca gaa gtc aag gag aaa gga atg gct gct ctt ccc agg     816
Lys Met Phe Pro Glu Val Lys Glu Lys Gly Met Ala Ala Leu Pro Arg
            260                 265                 270
```

```
ctc att gcc ttc acg tct gaa cat agt cat ttt tct ctc aag aag gga      864
Leu Ile Ala Phe Thr Ser Glu His Ser His Phe Ser Leu Lys Lys Gly
        275                 280                 285 gct gca gcc tta ggg att gga aca gac agc gtg att ctg att aaa tgt      912
Ala Ala Ala Leu Gly Ile Gly Thr Asp Ser Val Ile Leu Ile Lys Cys
        290                 295                 300 gat gag aga ggg aaa atg att cca tct gat cct gaa aga agg att ctt      960
Asp Glu Arg Gly Lys Met Ile Pro Ser Asp Pro Glu Arg Arg Ile Leu
305                 310                 315                 320 gaa gcc aaa cag aaa ggg ttt gtt cct ttc ctc gtg agt gcc aca gct     1008
Glu Ala Lys Gln Lys Gly Phe Val Pro Phe Leu Val Ser Ala Thr Ala
                325                 330                 335 gga acc acc gtg tac gga gca ttt gac ccc ctc tta gct gtc gct gac     1056
Gly Thr Thr Val Tyr Gly Ala Phe Asp Pro Leu Leu Ala Val Ala Asp
        340                 345                 350 att tgc aaa aag tat aag atc tgg atg cat gtg gat gca gct tgg ggt     1104
Ile Cys Lys Lys Tyr Lys Ile Trp Met His Val Asp Ala Ala Trp Gly
        355                 360                 365 ggg gga tta ctg atg tcc cga aaa cac aag tgg aaa ctg agt ggc gtg     1152
Gly Gly Leu Leu Met Ser Arg Lys His Lys Trp Lys Leu Ser Gly Val
370                 375                 380 gag agg gcc aac tct gtg acg tgg aat cca cac aag atg atg gga gtc     1200
Glu Arg Ala Asn Ser Val Thr Trp Asn Pro His Lys Met Met Gly Val
385                 390                 395                 400 cct ttg cag tgc tct gct ctc ctg gtt aga gaa gag gga ttg atg cag     1248
Pro Leu Gln Cys Ser Ala Leu Leu Val Arg Glu Glu Gly Leu Met Gln
                405                 410                 415 aat tgc aac caa atg cat gcc tcc tac ctc ttt cag caa gat aaa cat     1296
Asn Cys Asn Gln Met His Ala Ser Tyr Leu Phe Gln Gln Asp Lys His
                420                 425                 430 tat gac ctg tcc tat gac act gga gac aag gcc tta cag tgc gga cgc     1344
Tyr Asp Leu Ser Tyr Asp Thr Gly Asp Lys Ala Leu Gln Cys Gly Arg
        435                 440                 445 cac gtt gat gtt ttt aaa cta tgg ctg atg tgg agg gca aag ggg act     1392
His Val Asp Val Phe Lys Leu Trp Leu Met Trp Arg Ala Lys Gly Thr
        450                 455                 460 acc ggg ttt gaa gcg cat gtt gat aaa tgt ttg gag ttg gca gag tat     1440
Thr Gly Phe Glu Ala His Val Asp Lys Cys Leu Glu Leu Ala Glu Tyr
465                 470                 475                 480 tta tac aac atc ata aaa aac cga gaa gga tat gag atg gtg ttt gat     1488
Leu Tyr Asn Ile Ile Lys Asn Arg Glu Gly Tyr Glu Met Val Phe Asp
                485                 490                 495 ggg aag cct cag cac aca aat gtc tgc ttc tgg tac att cct cca agc     1536
Gly Lys Pro Gln His Thr Asn Val Cys Phe Trp Tyr Ile Pro Pro Ser
                500                 505                 510 ttg cgt act ctg gaa gac aat gaa gag aga atg agt cgc ctc tcg aag     1584
Leu Arg Thr Leu Glu Asp Asn Glu Glu Arg Met Ser Arg Leu Ser Lys
        515                 520                 525 gtg gct cca gtg att aaa gcc aga atg atg gag tat gga acc aca atg     1632
Val Ala Pro Val Ile Lys Ala Arg Met Met Glu Tyr Gly Thr Thr Met
        530                 535                 540 gtc agc tac caa ccc ttg gga gac aag gtc aat ttc ttc cgc atg gtc     1680
Val Ser Tyr Gln Pro Leu Gly Asp Lys Val Asn Phe Phe Arg Met Val
545                 550                 555                 560 atc tca aac cca gcg gca act cac caa gac att gac ttc ctg att gaa     1728
Ile Ser Asn Pro Ala Ala Thr His Gln Asp Ile Asp Phe Leu Ile Glu
                565                 570                 575 gaa ata gaa cgc ctt gga caa gat tta taa                             1758
Glu Ile Glu Arg Leu Gly Gln Asp Leu *
                580                 585
```

<210> SEQ ID NO 8
<211> LENGTH: 585
<212> TYPE: PRT
<213> ORGANISM: Homo sapiens

<400> SEQUENCE: 8

Met Ala Ser Pro Gly Ser Gly Phe Trp Ser Phe Gly Ser Glu Asp Gly
 1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Gly Ser Gln Pro Pro
 50                  55                  60

Arg Ala Ala Arg Lys Ala Ala Cys Ala Cys Asp Gln Lys Pro Cys
 65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
290                 295                 300

Asp Glu Arg Gly Lys Met Ile Pro Ser Asp Pro Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
        355                 360                 365

Gly Gly Leu Leu Met Ser Arg Lys His Lys Trp Lys Leu Ser Gly Val

-continued

```
                370                 375                 380
Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
                405                 410                 415

Asn Cys Asn Gln Met His Ala Ser Tyr Leu Phe Gln Gln Asp Lys His
                420                 425                 430

Tyr Asp Leu Ser Tyr Asp Thr Gly Asp Lys Ala Leu Gln Cys Gly Arg
                435                 440                 445

His Val Asp Val Phe Lys Leu Trp Leu Met Trp Arg Ala Lys Gly Thr
            450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
                500                 505                 510

Leu Arg Thr Leu Glu Asp Asn Glu Glu Arg Met Ser Arg Leu Ser Lys
                515                 520                 525

Val Ala Pro Val Ile Lys Ala Arg Met Met Glu Tyr Gly Thr Thr Met
                530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
                580                 585
```